United States Patent
Vinayagamoorthy

(10) Patent No.: US 11,028,442 B2
(45) Date of Patent: Jun. 8, 2021

(54) SIMULTANEOUS DETECTION OF MULTIPLE NUCLEIC ACID TEMPLATES USING MODIFIED PRIMERS

(71) Applicant: Bio-ID Diagnostic Inc., Edmonton (CA)

(72) Inventor: Thuraiayah Vinayagamoorthy, Greensboro, NC (US)

(73) Assignee: Bio-ID Diagnostic Inc., Edmonton (CA)

(*) Notice: Subject to any disclaimer, the term of this patent is extended or adjusted under 35 U.S.C. 154(b) by 0 days.

(21) Appl. No.: 16/521,965

(22) Filed: Jul. 25, 2019

(65) Prior Publication Data
US 2020/0032342 A1 Jan. 30, 2020

(30) Foreign Application Priority Data
Jul. 27, 2018 (EP) .................................. 18185987

(51) Int. Cl.
*C12Q 1/68* (2018.01)
*C12Q 1/6883* (2018.01)

(52) U.S. Cl.
CPC ...... *C12Q 1/6883* (2013.01); *C12Q 2600/112* (2013.01); *C12Q 2600/156* (2013.01)

(58) Field of Classification Search
None
See application file for complete search history.

(56) References Cited

U.S. PATENT DOCUMENTS

| | | |
|---|---|---|
| 8,754,191 B2 | 6/2014 | Nielsen |
| 8,771,965 B2 | 7/2014 | Sarkar |
| 8,788,215 B2 | 7/2014 | Chakraborty |
| 8,828,391 B2 | 9/2014 | Denis |
| 9,005,425 B2 | 4/2015 | Burrows |

FOREIGN PATENT DOCUMENTS

WO   WO0020628   4/2000

OTHER PUBLICATIONS

Sanchez et al., Multiplex PCR and minisequencing of SNPs—a model with 35 Y chromosome SNPs, Forensic Sci Int. Oct. 14, 2003; 137(1)74-84. doi: 10.1016/s0379-0738(03)00299-8.*
Ebili et al., "Squirrel" Primer-Based PCR Assay for Direct and Targeted Sanger Sequencing of Short Genomic Segments, J Biomol Tech. Sep. 2017; 28(3): 97-110. Published online Jun. 6, 2017.*
Binladen et al., 5'-tailed sequencing primers improve sequencing quality of PCR products, Biotechniques. Feb. 2007; 42(2):174, 176. doi: 10.2144/000112316.*
Kieleczawa, Fundamentals of Sequencing of Difficult Templates—An Overview, J Biomol Tech. Jul. 2006; 17(3): 207-217.*
Applied Biosciences, Sanger Troubleshooting Guide, Chapter 8 in DNA Sequencing by Capillary Electrophoresis Chemistry Guide, May 2009.*

(Continued)

*Primary Examiner* — Aaron A Priest

(57) ABSTRACT

The invention refers to a method of detecting one or more deoxyribose nucleotide (e.g. DNA) template(s) in a heterogenous sample by generation of template specific surrogate nucleotide sequences. This invention is applied to but not restricted in detecting genetic variations including cancer markers and pathogens.

4 Claims, 7 Drawing Sheets

Specification includes a Sequence Listing.

(56) References Cited

OTHER PUBLICATIONS

ThermoFisher, PCR for Sanger Sequencing, available at https://www.thermofisher.com/us/en/home/life-science/sequencing/sanger-sequencing/sanger-dna-sequencing/pcr-sanger-sequencing.html, accessed Aug. 14, 2020.*
Vinayagamoorthy et al., Can detection of Braf p. V600E mutation be improved? Comparison of allele specific multiplex sequencing to present tests, Journal of Solid Tumors 2017, vol. 7, No. 2, Apr. 12, 2017.*
Scheen et al., Use of allele-specific sequencing primers is an efficient alternative to PCR subcloning of low-copy nuclear genes, Mol Ecol Resour. Jan. 2012;12(1): 128-35. doi: 10.1111/j.1755-0998.2011.03070.x. Epub Sep. 22, 2011.*
Vinayagamoorthy et al., Detection of EGFR deletion using unique RepSeq technology, Manuscript,, doi: https://doi.org/10.1101/584045, Mar. 10, 2019.*
Response to European patent application No. 18185987.7, dated Jul. 28, 2020.*
Marie B., et al. Assessment of EGFR Mutation Status in Lung Adenocarcinoma by Immunohistochemistry Using Antibodies Specific to the Two Major Forms of Mutant EGFR. Journal of Molecular Diagnostics, 2010.Vol. 12, No. 2, March.
Nyren, Petersson and Uhlen (1993) "Solid Phase DNA Minisequencing by an Enzymatic Luminometric Inorganic Pyrophosphate Detection Assay" Analytical Biochemistry 208 (1), 171-175.
Sam Behjati and Patrick S Tarpey What is next generation sequencing? Arch Dis Child Educ Pract Ed. Dec. 2013; 98 (6): 236-238.
Choi, YW et al. EGFR Exon 19 Deletion is Associated with Favorable Overall Survival After First-line Gefitinib Therapy in Advanced Non-Small Cell Lung Cancer Patients. Am J Clin Oncol. Apr. 2018;41(4):385-390.
Banavali, Nilesh K.. "Partial Base Flipping is Sufficient for Strand Slippage near DNA Duplex Termini". Journal of the American Chemical Society. (2013), 135 (22): 8274-8282.13.
Richard Bayliss, Molecular mechanisms that underpin EML4-ALK driven cancers and their response to targeted drugs. Cell Mol Life Sci. 2016; 73: 1209-1224.
Bollag G, Tsai J, Zhang J, Zhang C, Ibrahim P, Nolop K, Hirth). "Vemurafenib: the first drug approved for BRAF-mutant cancer". Nature Reviews Drug Discovery. P (Nov. 11, 2012 (11): 873-886.
Steven Belenko, Detecting, Preventing, and Treating Sexually Transmitted Diseases Among Adolescent Arrestees: An Unmet Public Health Need. Am J Public Health. Jun. 2009; 99(6): 1032-1041. doi: 10.2105/AJPH.2007.122937.
Pagin,A, F Zerimech, J Leclerc, A Wacrenier, S Lejuene, C Descarpentries, F Escande, N Porchet, M-P Buisine. Evaluation of a new panel of six mononucleotide repeat markers for the detection of DNA mismatch repair deficient tumors. British Journal of Cancer vol. 108, pp. 2079-2087 May 28, 2013.
Saiki, R.; Scharf, S.; Faloona, F.; Mullis, K.; Horn, G.; Erlich, H.; Arnheim, N. "Enzymatic amplification of beta-globin genomic sequences and restriction site analysis for diagnosis of sickle cell anemia".(1985). Science. 230 (4732): 1350-1354.
Wiedmann, M; Wilson, WJ; Czajka, J; Luo, J; Barany, F; Batt, CA "Ligase chain reaction (LCR)—overview and applications". (Feb. 1994). PCR Methods and Applications. 3 (4): S51-64.
Bustin SA, Benes V, Garson JA, Hellemans J, Huggett J, Kubista M, Mueller R, Nolan T, Pfaffl MW, Shipley GL, Vandesompele J, Wittwer CT "The MIQE guidelines: minimum information for publication of quantitative real-time PCR experiments". Clinical Chemistry. (2009). 55 (4): 611-22.
Pollack JR; Perou CM; Alizadeh AA; Eisen MB; Pergamenschikov A; Williams CF; Jeffrey SS; Botstein D; Brown PO "Genome-wide analysis of DNA copy-number changes using cDNA microarrays". (1999). Nat Genet. 23 (1): 41-46.
Pettersson E, Lundeberg J, Ahmadian A (Feb. 2009). "Generations of sequencing technologies". Genomics. 93 (2): 105-11.
Southern, Edwin Mellor "Detection of specific sequences among DNA fragments separated by gel electrophoresis". (Nov. 5, 1975). Journal of Molecular Biology. 98 (3): 503-517.
Chehap et al., A dimorphic 4-bp repeat in the cystic fibrosis gene is in absolute inkage disequilibrium with the delta F508 mutation: implications for prenatal diagnosis and mutation origin. Am J Hum Genet. Feb. 1991; 48(2): 223-226.
Norikazu Matsuo. Association of EGFR Exon 19 Deletion and 5 EGFR-TKI Treatment Duration with Frequency of T790M Mutation in EGFR-Mutant Lung Cancer Patients. Sci Rep. 2016; 6: 36458.
Shaw, A.T and Jeffrey A. Engelman. ALK in Lung Cancer: Past, Present, and 15 Future. J Clin Oncol. Mar. 10, 2013; 31(8): 1105-1111.
Bubendorf, L et al., Testing for ROS1 in non-small cell lung cancer: a review with recommendations. Virchows Arch. 2016; 469(5): 489-503.
Snehal Dabir et al., RET Mutation and Expression in Small-Cell Lung Cancer. Journal of Thoracic Oncology. vol. 9, Issue 9, Sep. 2014, pp. 1316-1323.
Su Jin Lee et al., NTRK gene amplification in patients with metastatic cancer. Precision and Future Medicine 2017; 1(3): 129-137.
Li K, Yin R, Wang D, Li Q. Human papillomavirus subtypes distribution among 2309 cervical cancer patients in West China. Oncotarget. Apr. 25, 2017;8(17):28502-28509. doi: 10.18632/oncotarget.16093.
G Pennchery, D Nojima, R Goharderakhshan, Y Tanaka, J Alonzo, R Dahiya Microsatellite instability of dinucleotide tandem repeat sequences is higher than 30 trinucleotides, tetranucleotide and pentanucleotide repeat sequences in prostate cancer. International Journal of Oncology. Jun. 1, 2000, pp. 1203-1212 https://doi.org/10.3892/ijo.16.6.1203.
Oliver J, et al., Reduced penetrance alleles for Huntington's disease: a multi-center direct observational study. J Med Genet. Mar. 2007; 44(3): e68.
Sartor O, Dong Y. Androgen receptor variant 7: an important predictive biomarker in castrate resistant prostate cancer. Asian J Androl. May-Jun. 2015;17(3):439-40. doi: 10.4103/1008-682X.145069.
McNamara-Schroeder K, Olonan C, Chu S, Montoya MC, Alviri M, Ginty S, Love J.J. DNA fingerprint analysis of three short tandem repeat (STR) loci for biochemistry and forensic science laboratory courses. Biochem. Mol. Biol. Educ. Sep. 2006;34(5):378-83. Doi:10.1002/bmb.2006.494034052665.
Kosaka, T et al., Response heterogeneity of EGFR and HER2 exon 20 insertions to covalent EGFR and HER2 inhibitors. Cancer Res. May 15, 2017; 77(10): 2712-2721.
Reungwetwattana.T and Sai-Hong Ignatius Ou. MET exon 14 deletion (METex14): finally, a frequent-enough actionable oncogenic driver mutation in non-small cell lung cancer to lead MET inhibitors out of "40 years of wilderness" and into a clear path of regulatory approval. Transl Lung Cancer Res. Dec. 2015; 4(6): 820-824.
Beatriz S obrinoa, Maria BriOna, Angel Carracedo. SNPs in forensic genetics: a review on SNP typing methodologies. Forensic Science International 154 (2005) 181-194.
Jacob Yo, Katie S.L. Hay, Dilanthi Vinayagamoorthy, Danielle Maryanski, Mark Carter, Joseph Wiegel, Thuraiayah Vinayagamoorthy. Detection of BRAF mutations from solid tumors using TumorplexTM technology. MethodX 2: 2015, 316-322.

* cited by examiner

SEQUENCE LISTING

<160> NUMBER OF SEQ ID NOS: 13

<210> SEQ ID NO 1
<211> LENGTH: 23
<212> TYPE: DNA
<213> ORGANISM: Homo sapiens

<400> SEQUENCE: 1
gtgtgattcg tggagcccaa cag                      23

<210> SEQ ID NO 2
<211> LENGTH: 53
<212> TYPE: DNA
<213> ORGANISM: Homo sapiens

<400> SEQUENCE: 2

```
gtattattat tattattatt attattactc acatcgagga tttccttgtt ggc        53

<210> SEQ ID NO 3
<211> LENGTH: 26
<212> TYPE: DNA
<213> ORGANISM: Homo sapiens

<400> SEQUENCE: 3
ctcacatcga ggatttcctt gttggc                                      26

<210> SEQ ID NO 4
<211> LENGTH: 28
<212> TYPE: DNA
<213> ORGANISM: Homo sapiens

<400> SEQUENCE: 4
aaagttaaaa ttcccgtcgc tatcaagg                                    28

<210> SEQ ID NO 5
<211> LENGTH: 45
<212> TYPE: DNA
<213> ORGANISM: Homo sapiens

<400> SEQUENCE: 5 aaaagggtt ttcttaagcg tcgatggagg agtttgtaaa tgaag                   45

<210> SEQ ID NO 6
<211> LENGTH: 30
<212> TYPE: DNA
<213> ORGANISM: Homo sapiens

<400> SEQUENCE: 6
tcaaagaatg gtcctgcacc agtaatatgc                                  30

<210> SEQ ID NO 7
<211> LENGTH: 32
<212> TYPE: DNA
<213> ORGANISM: Homo sapiens

<400> SEQUENCE: 7
ccagttgact gcagacctgt atcgtaatga ac                               32

<210> SEQ ID NO 8
<211> LENGTH: 42
<212> TYPE: DNA
<213> ORGANISM: Chlamydia trachomatis

<400> SEQUENCE: 8
tcggttttga taatttgtcc ttaacttggg aataacggtt gg                    42

<210> SEQ ID NO 9
<211> LENGTH: 25
<212> TYPE: DNA
<213> ORGANISM: Chlamydia trachomatis

<400> SEQUENCE: 9
ccctagagcc ttcatcacac acgcg                                       25

<210> SEQ ID NO 10
<211> LENGTH: 34
<212> TYPE: DNA
<213> ORGANISM: Chlamydia trachomatis

<400> SEQUENCE: 10
```

```
tatgcccaaa tatcgccaca ttcggtatta gcgg                                34

<210> SEQ ID NO 11
<211> LENGTH: 30
<212> TYPE: DNA
<213> ORGANISM: Neisseria gonorrhoeae

<400> SEQUENCE: 11
gctttcggcg aggatttgta cgaagagctg                                     30

<210> SEQ ID NO 12
<211> LENGTH: 21
<212> TYPE: DNA
<213> ORGANISM: Neisseria gonorrhoeae

<400> SEQUENCE: 12
ttgcccgcgc cgttgatacc g                                              21

<210> SEQ ID NO 13
<211> LENGTH: 25
<212> TYPE: DNA
<213> ORGANISM: Neisseria gonorrhoeae

<400> SEQUENCE: 13
cccatatcgc cggtaatcag cacgg                                          25
```

SIMULTANEOUS DETECTION OF MULTIPLE NUCLEIC ACID TEMPLATES USING MODIFIED PRIMERS This application claims priority to co-pending and commonly assigned EPO Patent Application No. 18185987 filed Jul. 27, 2018 for Simultaneous Detection of Multiple Nucleic Acid Templates Using Modified Primers. This EPO application is incorporated by reference in its entirety.

FIELD OF INVENTION

This invention is for molecular diagnosis in clinical, veterinary, food safety and environmental testing. The applications of this invention include, but are not limited to, human and animal disease conditions detecting genetic variations, including cancer markers, DNA fingerprinting for forensic applications, paternity testing, and detection and speciation of pathogens.

BACKGROUND INFORMATION

With the elucidation of the structure of DNA and the completion of the human genome project, research and clinical studies were pursued to identify genetic variances, known as mutations, which are correlated with disease conditions. Therefore, there is a need to detect genetic variances for diagnosis, prognosis, treatment and overall management of patients. Over the past few decades, there have been numerous medical and scientific reports claiming association of genetic variances with specific disease conditions (1). These genetic variances could be either germline mutations (hereditary), or somatic mutations (acquired). Both germline and somatic mutations include nucleotide substitutions known as single nucleotide polymorphism (SNP), deletions or additions (insertions) of one or more nucleotides, fusion of segments from different genes, fusion of RNA segments from different genes, and copy number variations. Further, the same genetic variances are found in either one allele (loss of heterozygosity) or both alleles (homozygosity) of eukaryotic genomes, including that of the human genome.

Presently, there are several sequencing platforms, including Sanger sequencing, pyrosequencing and next generation sequencing (2,3). Out of all sequencing methods, Sanger sequencing is considered the 'Gold Standard', a method of reference, and confirmatory for identifying a DNA or an RNA template. Traditional use of Sanger sequencing is designed to sequence a single homogenous DNA template. Standard nucleic acid sequencing consists of a sequencing primer that anneals to one of the strands of the DNA template, and DNA polymerase randomly incorporating both dideoxynucleosides and deoxynucleotides, generating a series of truncated, single stranded DNA with the nucleotide at the 3' end comprising one of the four fluorophores attached to the dideoxynucleosides. When these labeled truncated molecules are separated through capillary electrophoresis, they pass the CCD camera and the fluorophore signals are then recorded and analyzed to indicate the order of the nucleotide sequence of the nucleic acid template.

However, nucleic templates in clinical samples are heterogeneous in that they include, for example, a mixture of organisms, each with their respective genomes; and in a cancer samples, there is a mixture of normal cells known as wild type, and abnormal cells or transformed cells, which could carry different genetic variations. Hence, there is a need to identify the genetic variations of the abnormal cells in the midst of overwhelming normal cells with specific genetic variations in such heterogeneous samples.

Some of these nucleic acid templates include genetic variants such as deletion of one or more nucleotides, addition of one or more nucleotides known as insertion, fusion of segments of nucleic acid from other parts of the genome and/or from another genome, and nucleotide substitution where one or more nucleotides are different (4, 5,6,7). Deletion, insertion, fusion and substitution are genetic variations that could occur in genomes of all life forms. Deletion is where a stretch of the DNA or RNA is deleted, for example, during replication. Insertion is where a stretch of DNA or RNA is added to the genome, for example, also during replication. Fusion is where DNA or RNA segments from two or more genes come together, called gene fusion. Fusion occurs, for example, during transcription known as fusion transcript. Substitution is where a (one or more) nucleotide is replaced by another one (one or more), for example during replication. If more than one nucleotide is replaced, the replaced nucleotides are directly next to each other or separated by one or more non-replaced nucleotide(s). In addition to genetic variations, there are also clinical samples that carry genomes of different species. For example, microbial organisms such as sexually transmitted diseases in a sample that carries heterogeneous genomes. Hence there is a need to identify microorganism that is causing the infection (8).

Detection of individual nucleic acid templates by standard Sanger sequencing with two or more genetic materials (nucleic acid templates) in the same sample can cause difficulty in interpreting results. For example, in a sample with two different alleles, one allele comprising a deletion and the other allele the wild type, using the same sequencing primer, both the nucleotide sequences will overlap, resulting in mixed base calls where no meaningful nucleotide sequence is derived. Similarly, if the sample is from a heterozygous template of two different alleles, one allele with an insertion and the other the wild type, using the same sequencing primer, both the nucleotide sequences overlap, resulting in mixed calls where no meaningful nucleotide sequence is derived. This invention provides a novel modification to solve the above dilemma. Using a surrogate site, nucleic templates with genetic variations in a heterozygous sample are detected. This invention is comprised of modifications of one or more primers used (e.g. uppers primer and lower primers) in the amplification step (e.g. polymerase chain reaction or ligase chain reaction or ligase polymerization reaction) and the sequencing step.

SUMMARY OF INVENTION

This invention refers to a method of detecting one or more nucleic acid templates, either dideoxy ribose (DNA) and/or ribose nucleic acid (RNA), from a heterogeneous sample. The heterogeneous samples could carry one or more categories of nucleic acid templates from different species and/or genetic variations of the same species. The method of invention is comprised of the steps of amplifying specific segments of the template nucleic acid and sequencing the amplification product (amplicon) to identify specific nucleic acid template(s) and/or specific genetic variations that they carry. This process is achieved but not limited by using a surrogate nucleotide sequence that comes into play during the amplification step.

In one aspect of the invention, a surrogate nucleotide sequence is used where modification is made to one or both (upper primer and lower primer) of the oligonucleotide primers used in the amplification of specific segments of nucleic acid templates. For example, the modification comprises a lower primer that at its 5' end carries a detection region with a repetitive pattern of one or more nucleotides, followed by an indicator region, which also has a repetitive pattern of one or more nucleotides that is distinct from the nucleotides of the detection region. The lower primer anneals downstream of the target segment (e.g. region of genetic variation) to the DNA strand which is complimentary to the lower primer and is extended by DNA polymerase, generating a single stranded DNA template. Using a sequencing reaction, the sequencing primer anneals at the 3' end of the extended single stranded DNA template, generating a nucleotide sequence that includes the detection region and the indicator region. The nucleotide sequences generated are automatically aligned and displayed on an electropherogram. When two variant templates, one with the deletion and the other with the wild type, are sequenced simultaneously, the nucleotide sequence from the deletion will be shorter than the one from the wild type. The location of an indicator nucleotide region within in the detection region thereby identifies the template with the deletion.

In another aspect of the invention, an upper primer carries the detection and the indicator region at its 5' end, and anneals upstream of the mutation, asymmetrically amplifying a segment of the wild type template encompassing the corresponding DNA segment of interest, generating wild type amplicons, and amplifying the corresponding segment of the mutant template, generating mutant amplicons. These two categories of amplicons are sequenced using a sequencing primer that anneals in the wild type amplicons downstream of the segment of interest and anneals in the mutant amplicons downstream of the segment of interest.

In another aspect of the invention, both the upper primer and a lower primer are used in the amplification, and either one or both primers carry the detection region and the indicator region.

In another aspect of the invention, in order to obtain better resolution of the nucleotide signals, copies of the segment of interest of the templates are produced by amplification, during which the annealing and extension of the primer occur alternatively a number of times, known as asymmetric polymerase chain reaction. Asymmetric amplification could be carried out either by using the lower primer that anneals downstream of the target segment, followed by sequencing in which the sequencing primer anneals upstream of the target segment, or by using an upper primer that anneals upstream of the target segment and is followed by sequencing in which the sequencing primer anneals downstream of the target segment, generating a corresponding single stranded amplicon. Similarly, amplification could be symmetrical (double stranded amplification), in which both lower and upper primers are used, where the lower primer anneals to one strand of the DNA duplex downstream of the target segment and the upper primer anneals upstream of the target segment to its complimentary DNA stand.

In some aspect of the invention, amplification of specific segments of the template is carried out by ligase chain reaction where two primers anneal to the same DNA strand of the template one nucleotide apart (9). Further, ligase chain reaction could be performed either asymmetrically, where both the primers anneal to the sense strand, end-to-end one nucleotide apart, or an additional two primers anneal at the same time to the anti-sense stand, one nucleotide apart on the template, as in symmetrical double stranded amplification.

In another aspect of the invention, in order to enhance the amplification of the specific genetic variant, the annealing sites of the lower primer and/or the upper primer to the corresponding DNA template is chosen in relation to the specific genetic variations of the target segment. Further, in order to enhance detection of the target segment, the annealing sites of the sequencing primers in the target segment are chosen in relation to the genetic variations they carry. Details of these aspects are described below in various embodiments.

There are different forms of genetic variations, known as mutations, where there are changes to the nucleotide sequences that are carried by specific target segments compared to the wild type. The following embodiments outline the detection of these different mutations and genomes.

In an embodiment of the invention, wherein one of the nucleic templates has a deletion region, known as a deletion template, compared to the corresponding wild type DNA template that does not have the deletion region, and instead has a corresponding wild type region, the first lower primer anneals to the deletion template downstream of the deletion region, and the second lower primer anneals to the wild type template downstream of the wild type region, and using polymerase chain reaction amplifies a segment of the DNA, generating corresponding single stranded amplicons. These two categories of amplicons are sequenced using the same sequencing primer that anneals to the extended deletion template upstream of the deletion region and anneals to the extended wild type template upstream of the wild type region. The electropherogram aligns the generated nucleotide sequences, with two indicator regions, one at the far end of the electropherogram, the wild type template, and the other indicator region within the detection region that identifies the deletion template.

In another aspect of the above embodiment, the amplification uses an upper primer that anneals upstream of the segment of interest and uses the lower primer that binds downstream of the target of interest, generating a double stranded amplicon.

In another aspect of the above embodiment, in the amplification step the lower primer anneals to the deletion template across the deletion region.

In another aspect of the above embodiment, in the amplification step the upper primer anneals to the deletion template across the deletion region.

In another aspect of the above embodiment, where two sequencing primers are used, one anneals to the wild type amplicon upstream of the wild type region. The other anneals to the deletion amplicon, across the deletion region, wherein part of the sequencing primer anneals upstream of the deletion region and the remaining part anneals downstream of the deletion region. A part of a primer in any context for example invention comprises, for example 2 to 12 nucleotides, e.g., 2, 3, 4, 5, 6, 7, 8, 9, 10, 11 or 12 nucleotides. An example of a primer annealing around a deletion region is the following:

```
EGFR Del 746-A750
Upper primer
TATCAA................................AA-3'

TATCAAGGAATTAAGAGAAGCAACATC
```

In another aspect of the above embodiment, there is more than one deletion template, each with its own deletion region. By using mutant template-specific lower primers, and corresponding sequencing primers, locating the presence of mutant template-specific indicator regions in the detection region identifies each of the mutant templates.

In another embodiment of the invention, wherein one of the nucleic templates, having one or more additional nucleotides, known as an insertion template, compared to the corresponding wild type region of the wild type DNA template that that does not have the insertion region, the lower primer anneals to the insertion template downstream of the insertion region, and anneals to the wild type template downstream of the wild type region, and amplifies a segment of the DNA, generating corresponding single stranded amplicons. These two categories of amplicons are sequenced using a sequencing primer that anneals to the extended insertion template upstream of the insertion region and to the extended wild type template upstream of the wild type region. The electropherogram aligns the generated nucleotide sequences, with two indicator regions, one at the far end of the electropherogram, the insertion template, and the other indicator region within the detection region that identifies the wild type template.

In another aspect of the above embodiment, in the amplification step, where the lower primer anneals to the inserted template where part of the 3' end of the lower primer is within the insertion region, and rest of the first lower primer is downstream of the insertion region.

In another aspect of the above embodiment, in the amplification step, the entire first lower primer anneals within the insertion region.

In another aspect of the above embodiment, in the amplification step, the lower primer anneals to where part of its 5' end is within the inserted region and the remainder of the lower primer anneals downstream of the inserted region.

In another aspect of the above embodiment, the upper primer that carries the detection and the indicator region at its 5' end, anneals upstream of the insertion region and asymmetrically amplifies a segment of the wild type template, generating wild type amplicons, and amplifies the corresponding segment of the mutant template, generating mutant amplicons.

In another aspect of the above embodiment, in the amplification step, the upper primer anneals in the inserted template where part of the 5' end is upstream of the insertion region, and the remainder of the upper primer is within the insertion region.

In another aspect of the above embodiment, in the amplification step, the entire upper primer anneals within the insertion region.

In another aspect of the above embodiment, in the amplification step, the upper primer anneals where part of its 5' end is within the inserted region and the rest is downstream of the inserted region.

In another aspect of the above embodiment, in the amplification step, a lower primer anneals to the insertion template downstream of the insertion region, and to the wild type template downstream of the wild type region, generating corresponding double stranded amplicons.

In another aspect of the above embodiment, in the sequencing step, two sequencing primers are used, one anneals to the wild type, and the other sequencing primer anneals to the insertion amplicons with its 3' end within the insertion region and its 5' end downstream of insertion region.

In another aspect of the above embodiment, the sequencing primer anneals to the insertion amplicons, where the entire sequencing primer anneals within the insertion region.

In another aspect of the above embodiment, in the sequencing step, the sequencing primer anneals to the insertion amplicons, with its 3' end downstream of the insertion region and its 5' end within the insertion region.

In another aspect of the above embodiment, there is more than one mutant template, each with its own insertion region. By using mutant template-specific lower primers, and corresponding sequencing primers, locating the presence of mutant template specific indicator regions in the detection region identifies each of the mutant templates.

Another embodiment of the invention identifies a fusion template (DNA) that comprises a segment A from a wild type template, joined at its 3' end to a 5' end of segment B from another genome, known as fusion region. In the corresponding wild type segment A and segment C of the wild type are joined by a wild type region. Two lower primers are used, in which one lower primer anneals to the sense strand of segment B of the fusion template downstream of the fusion region, and the other lower primer anneals to the sense strand of segment C of the wild type template downstream of the wild type region. Amplification is by polymerase chain reaction and sequencing with a sequencing primer that anneals to segment A of the wild type and to segment A of the fusion template. The primers that anneal to segment A of the wild type template and to segment A of the fusion template at its 5' end, comprise a detection region of repeated nucleotides, wherein the number of repeated nucleotides is identical or differ from each other, and an identification region is comprised of one or more repetitive nucleotides that are different to that of the detection region.

In another aspect of the above embodiment, the primers that anneal to segment C of the wild type template and segment B of the fusion template at its 5' end, comprise a detection region of repeated nucleotides, wherein the number of repeated nucleotides is identical or differ from each other, and an identification region is comprised of one or more repetitive nucleotides that are different to that of the detection region.

In another aspect of the above embodiment, double stranded amplicons of the fusion template and the wild type templates are generated using an additional set of primers that bind to the anti-sense strand, by polymerase chain reaction, and the respective amplicons are sequenced.

In another aspect of the above embodiment, either the lower or the upper PCR primers anneal across the fusion region in the fusion template, and/or the sequencing primer anneals to the fusion template across the fusion region in the fusion template.

In another embodiment of the invention, a mutant template comprises a substitution region at a specific locus on the template that carries a different nucleotide to that of the wild type and/or to another corresponding template. An upper primer and the lower primer amplify a segment of the DNA template encompassing the substitution region, where the upper primer anneals upstream of the substitution region and the lower primer anneals downstream of the substitution region, and using allele specific sequencing primers (one or more), where the 3' end of the sequencing primer anneals at the substitution region, generating a nucleotide sequence that corresponds to a nucleotide sequence downstream of the substitution region, and the generated nucleotide sequence is complimentary to the lower primer, the homopolymer detection region and the indicator region at the 5' end.

In another aspect of the above embodiment, the amplification is carried out either by polymerase chain reaction or ligase chain reaction, using either the upper or lower primer, generating asymmetric amplification, or using both the upper and lower primers, as in symmetric double stranded amplification.

In another aspect of the above embodiment, the homopolymer detection region and the indicator region could be carried out by either upper or lower primers.

In another embodiment of the invention, wherein there is identification from a mixture of more than one species-specific genomic template, a template-specific upper primer and/or lower primer amplifies a species-specific segment of the respective template where the upper primer anneals upstream of the template specific region and the lower primer anneals downstream of the template specific region. The amplification is carried out either by polymerase chain reaction or ligase chain reaction, using one of the primers, generating asymmetric amplification, or using both the primers as in symmetric double stranded amplification. The homopolymer detection region and the indicator region could be carried by either by upper or lower primers. The amplicons are sequenced using species-specific sequencing primers that anneal within the respective amplicon, generating a nucleotide sequence, and different templates are identified by the specific location of the respective indicator regions in the detection region.

All documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

DETAILED DESCRIPTION OF THE INVENTION

Figure 1:
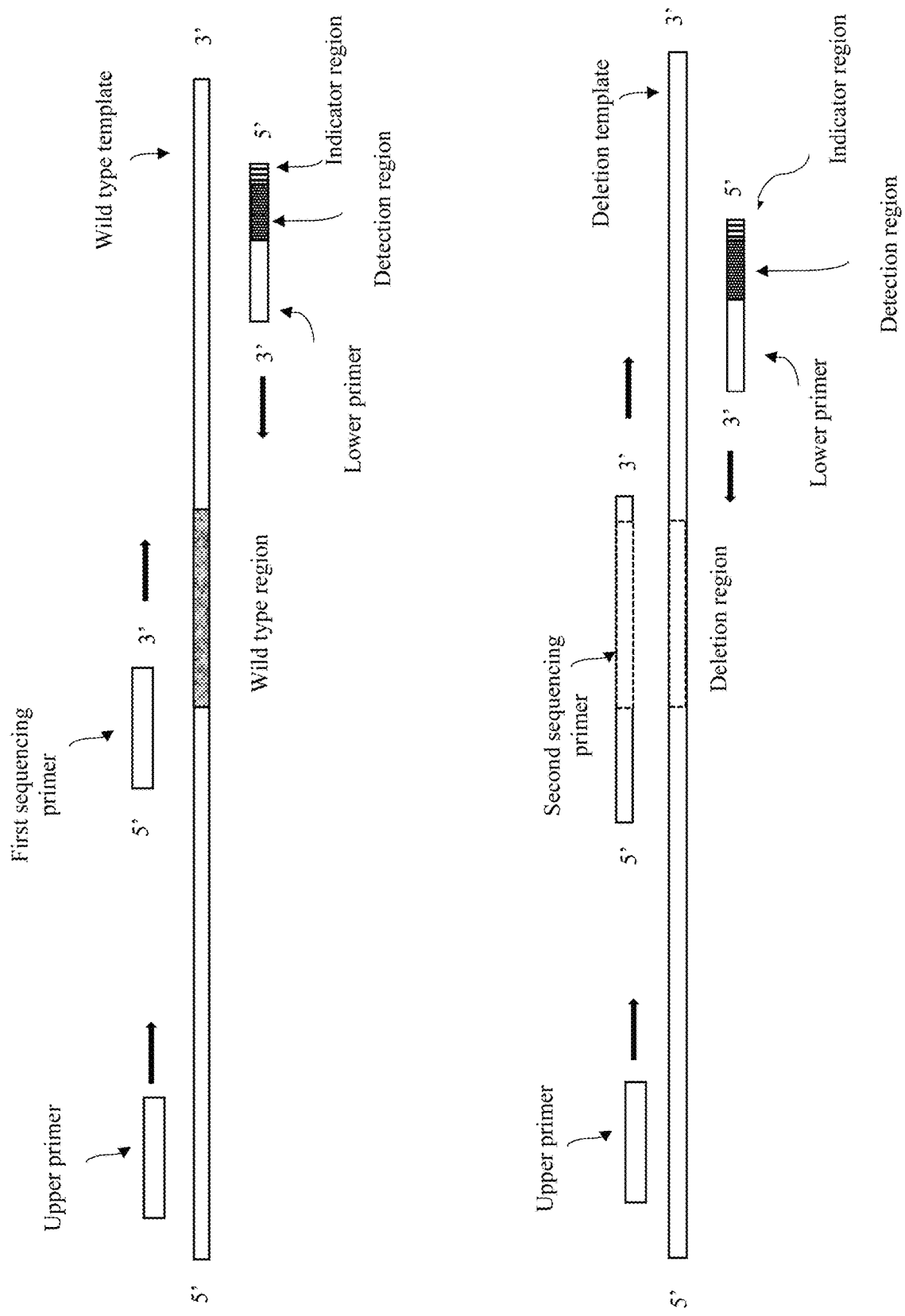
FIG. 1 illustrates the invention in identifying a mutant allele in a heterogeneous sample carrying a deletion segment compared to the wild type allele; indicating the construction of the modified lower primer with detection region and the indicator region, PCR primer annealing sites and the sequencing primer annealing sites.
Figure 2:
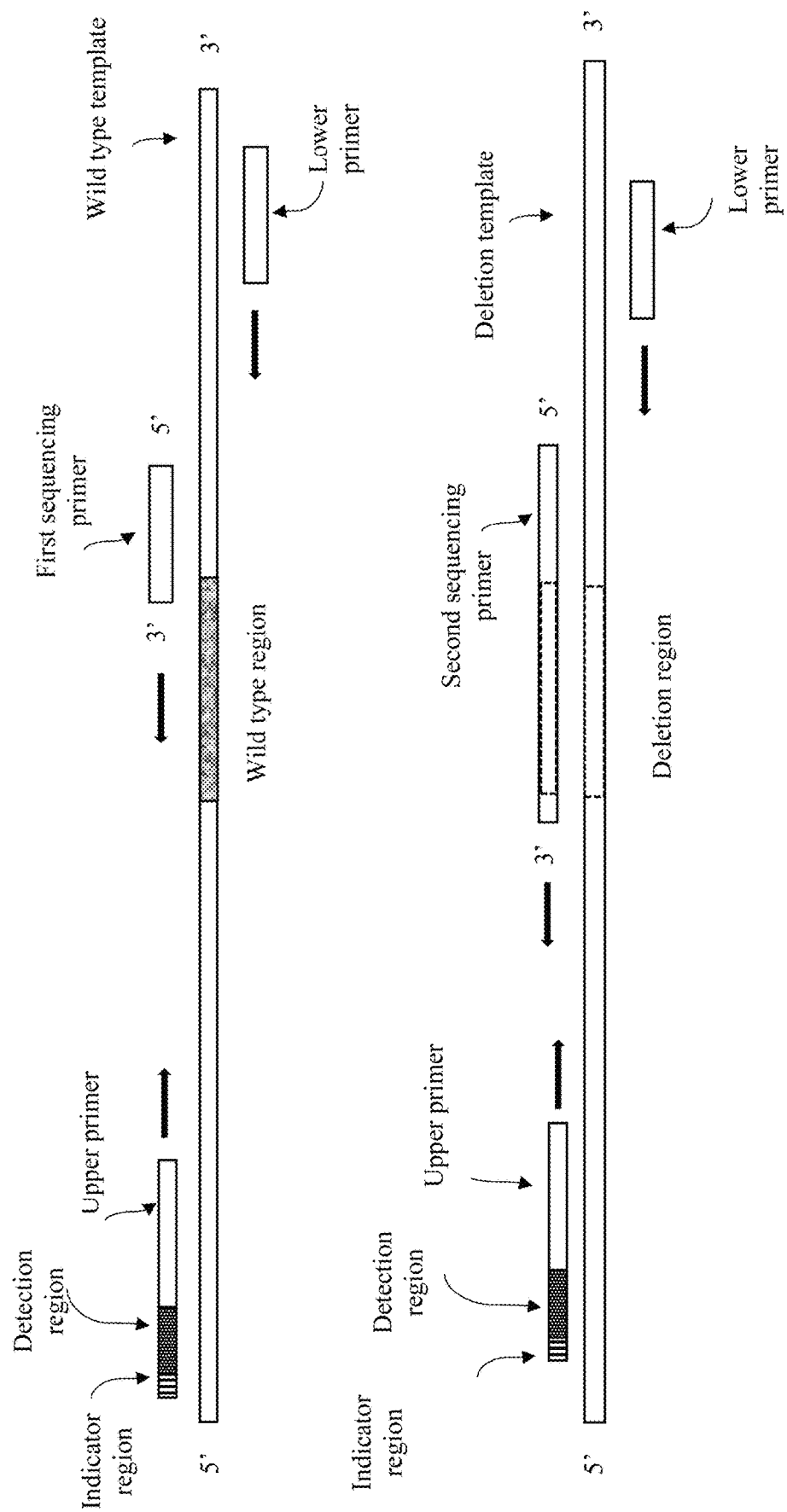
FIG. 2 illustrates the invention in identifying a mutant allele in a heterogeneous sample carrying a deletion segment compared to the wild type allele; indicating the construction of the modified upper primer with detection region and the indicator region, PCR primer annealing sites and the sequencing primer annealing sites.

A typical molecular diagnostic method includes three basic steps: Extraction of nucleic acid (DNA, RNA), an amplification step such as polymerase chain reaction by which specific nucleic acid segments are amplified, and an identification step. The extraction is a routine process, where the cells carrying the genetic materials are broken enzymatically and/or mechanically and the nucleic acid is purified using magnetic beads, filtration, centrifugation, etc. (10). Extraction is followed by an amplification step in which a specific segment of the DNA or RNA is amplified, for example by polymerase chain reaction or ligase chain reaction, using nucleic acid template specific primers (11,12). Such amplification could be asymmetric amplification using one primer, either a lower primer or an upper primer, generating single stranded amplicons, or could be symmetric amplification using both the lower and upper primers generating double stranded amplicons. Once the amplification is completed, the amplified products (i.e. amplicons) are identified by various methods including end-point PCR, real time PCR, micro-array analysis, mass spectrometry, or DNA sequencing (13,14,15). Two of the most common technologies presently used in detecting allele-specific nucleotides are Southern blotting using radio isotopes, and/or fragment analysis using fluorophores (16). Since the endpoint of the above methods is based on a single light signal, the authenticity of the original nucleic acid template is not verifiable. Further, in the above methods, since the amplicons could be the result of a nonspecific amplification, these identification methods are not confirmatory, leading to false positives. As an alternative, following amplification the amplicons can be sequenced, where the sequencing primer anneals within the amplicon, generating specific nucleotide sequences that can be verified and hence confirmed. The nucleotide sequence generated is analyzed by Sequencing Analysis and is displayed on an electropherogram.

The method of the invention includes nucleic acid extraction, which is either the extraction of total DNA, RNA or both, using standard procedures. There are several commercially available kits to extract DNA and RNA from clinical samples. Total nucleic acid extraction is followed by amplification, where more copies of the target of interest from nucleic acid templates are generated. Such amplification is carried out by a method such as polymerase chain reaction or ligase chain reaction. Further, the amplification could be either asymmetrical, using either a lower primer or an upper primer, or symmetrical where both the upper and lower primers are used together. In the following, the elements of the instant invention will be described in more detail.

The technical elements of the invention are listed below with specific embodiments. However, the features and invention steps may be combined in any manner and in any number to create additional embodiments. The variously described examples and embodiments should not be construed to limit the instant invention to only the explicitly described embodiments. This description should be understood to support and encompass embodiments which combine the explicitly described embodiments with any number of the disclosed elements. Furthermore, any permutations and combinations of all described elements in this application should be considered disclosed by the description of the instant application unless the context indicates otherwise.

Throughout this specification and the claims, unless the context requires otherwise, the word "comprise", and variations such as "comprises" and "comprising", will be understood to imply the inclusion of a stated member, integer or step or group of members, integers or steps but not the exclusion of any other member, integer or step or group of members, integers or steps. The terms "a" and "an" and "the" and similar reference used in the context of describing the invention (especially in the context of the claims) are to be construed to cover both the singular and the plural, unless otherwise indicated herein or clearly contradicted by the context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as", "for example"), provided herein is intended merely to better illustrate the invention and does not pose a limitation on the scope of the invention otherwise claimed. No language in the specification should be construed as indicating any non-claimed element essential to the practice of the invention.

The term "about" means a quantity, level, value, number, frequency, percentage, dimension, size, amount weight, length etc. that varies by as much as 10, 9, 8, 7, 6, 5, 4, 3, 2, 1% from a reference quantity, level, value, number, frequency, percentage, dimension, size, amount weight, length etc.

In one aspect of the invention, a surrogate nucleotide sequence is used where modification is made to one or both the oligonucleotide primers, used in the amplification of specific nucleic acid templates carrying specific genetic variations, known as mutations. As an example, a modification where the lower primer at its 5' end carries a detection region with a repetitive pattern of one or more nucleotides, (e.g. repetitive thymidine nucleotide). Further, there is an indicator region at the 5' end of the detection region, which comprises a single or repetitive nucleotide sequence that has a different nucleotide from the nucleotides of the detection region. For example, the indicator region carries a thymidine nucleotide that is distinct from the adenosine nucleotide of the detection region (Table1).

TABLE 1

Showing position of the indicator region on the electropherogram (Results)

| | Sequencing primer | Lower primer | Detection region | Indicator Region |
|---|---|---|---|---|
| Template 1 | TTTTTCGATGCG | CCGAGCCTTTC | A A A A A A A | A A A A TT |
| Template 2 | TTGGCCGGTCCA | CGTACTGGACC | A A A A A A T | T |
| Results | | | A A A A A A A/TA/TA A A | TT |

Further, the repetitive nucleotides in the detection region and/or indicator region could be comprised of two alternating nucleotides. For example, the detection region containing thymidine/adenosine, and the indicator region containing cytosine/guanidine. Hence, the repetitive nucleotide pattern of the indicator region could be made up of either one or more nucleotides, provided the nucleotides of the indicator region can be distinguishable when the indicator region is within the detection region of the reference template.

The above modifications are custom designed and are specific to the nucleic acid template tested. For example, if the genetic variant is an insertion of two nucleotide repeats then the detection region is of two nucleotide repeats. The number of repeat units in the detection region will be more than that of the genetic variant. For example, if the maximum insertion of nucleotides is ten nucleotides, then the repeat detection region will have more than ten nucleotides. Hence the number of nucleotides in the repetitive detection region is determined by the maximum number of nucleotide variants found in allele.

For example, Huntington's disease carries a three-nucleotide repeat, hence a homologous repetitive segment with a three-nucleotide repeat. The repeats of the nucleotide are, for example, independent of the condition in the number of 1 to 100, 2 to 95, 3 to 85, 4 to 80, 5 to 75, 6 to 70, 7 to 65, 8 to 60, 9 to 55, 10 to 50, 11 to 45, 12 to 40, 13 to 35, 14 to 30, or 15 to 25. The number of the repeats is for example 1, 2, 3, 4, 5, 6, 7, 8, 9, 10, 11, 12, 13, 14, 15, 20, 25, 30, 35, 40, 45, 50, 55, 60, 65, 70, 75, 80, 85, 90, or 95. At the distal end of the repetitive region there is an indicator region that will carry one or more nucleotides different from that of the homologous repetitive region wherein, for example 1, 2, 3, 4, 5, 6, 7, 8, 9, 10, 11, 12, 13, 14, 15, 20 or 25 nucleotides are different.

In one aspect of the invention, the lower primer anneals downstream of the target segment (e.g. region of genetic variation) to its complimentary DNA strand and is extended by DNA polymerase, generating single stranded extended DNA template. Following the extension, the extended DNA template is sequenced using a sequencing primer that anneals to the extended DNA template its 3' end (starting point) through the modified lower primer to the end of the indicator region. The nucleotide sequences generated has three segments; the first segment is from the 3' end of the sequencing primer to the beginning of the detection region, followed by the detection region and then the indicator region. The human genome is diploid and carries two alleles.

If both the alleles are wild type, then the extension from the lower primer will generate two identical extended single stranded DNA templates. When the extended single stranded DNA templates are sequenced simultaneously using a single sequencing primer, this generates two nucleotide sequences; one from each of the two alleles that will be identical. The nucleotide sequences are automatically aligned and displayed on an electropherogram and the electropherogram will not have any mixed base reads.

The above aspects of the invention are described in more details in various embodiments listed below.

A disease where the method of the instant invention is applicable for detection is cystic fibrosis, for example, where more than three nucleotide deletions are involved (17). Cystic fibrosis is an autosomal germline mutation in both alleles of the human genome under disease conditions, and a single allele mutation in carriers. The gene expresses cystic fibrosis transmembrane conductance regulator (CFTR) protein. The common mutation of the CFTR gene is, for example, the three-nucleotide deletion ΔF508 that results in the loss of amino acid phenylalanine at the 508 amino acid position. Although traditionally cystic fibrosis has been diagnosed by measuring blood levels of immunoreactive trypsinogen, presently cystic fibrosis diagnosis is carried out by molecular tests. This invention will be able to detect both single allele deletion and double allele deletions.

Moreover, the instant invention refers to the detection of genetic variations related to cancer. Apart from germline mutations, there are, for example, somatic mutations that occur during one's lifetime. Most of these mutations are associated with incidence and progression of cancer. This includes, for example, Epidermal growth factor receptor (EGFR) exon 19 in non-small cell lung cancer, which is detected before targeted therapy (18). It is also noted that in any of these cases there may be multiple variants (e.g. deletion in EGFR exon 19 may be 9 nucleotides, 15 nucleotides or any other number of nucleotides such as 10, 11, 12, 13, 14, 16, 17, 18, 19, 20, 21, 22, 23, 24, 25, 26, 27, 28, 29, 30, 31, 32, 33, 34, 35, 36, 37, 38, 39, 40, etc. Further, deletions can be located anywhere in Exon 19

Clinical samples such as cancer biopsy (Formalin Fixed Paraffin Embedded) could have heterogeneous cell populations, where some of the cells would have acquired somatic mutations. Further, the number of cells with somatic mutations in the sample could be low compared to the overwhelming number of wild type alleles.

Another embodiment of the invention is where one of the alleles has a deletion region, known as the deletion template, and the other allele, known as wild type allele, does not have the corresponding deletion region, known as wild type region (FIG. 1, 2). The lower primer with the detection region and the indicator region anneals to the wild type allele downstream of the wild type region and anneals to the deletion template downstream of the deletion region. Using DNA polymerase, the lower primer extends, generating two single stranded DNA templates; the one from the wild type template will have a complete sequence, whereas the one from the deletion template will have single stranded DNA without the deletion region. Both the extended single stranded DNA templates are sequenced simultaneously using the same sequencing primer that anneals to the deletion template upstream of the deletion region and anneals to the wild type template upstream of the wild type region generates two nucleotide sequences. The sequence generated from the deletion template will be shorter than that generated from the wild type template. Therefore, there will be an overlap of nucleotide sequences at the proximal end of the electropherogram and the individual nucleotide signals are not distinguishable. However, since sequences generated from both of the templates have the same repetitive nucleotides in their respective detection region, any overlap of nucleotide sequences in the detection region will be distinguishable and readable. For example, if there is a three nucleotide deletion (i.e. segment between 3' end of the sequencing primer to the 5' end of the modified lower primer), the nucleotide sequence generated from the deletion allele will be three nucleotides shorter than the nucleotide sequence generated by the wild type amplicon. This in turn moves the indicator region of the deletion sequence three places to left on the electropherogram. The three-nucleotide shift to the left in the electropherogram will fall within the detection region, overlapping with the nucleotides of the detection region. Since the detection region and the indicator regions are made up of different nucleotides, they emit different fluorescence signals, hence the indicator region is distinguishable from that of the detection region and confirms presence of deletion template in the sample. The extent of the deletion is determined by the difference in the nucleotide sequence divided by the units of the variation. For example, if the difference of the number of nucleotides between the indicator of the wild type and the indicator of the deletion template is twelve nucleotides, and the unit of deletion is three nucleotides, then the deletion template carries four units of the deletion.

In another aspect of the above embodiment in the amplification step an upper primer is included, which anneals to the deletion template upstream of the deletion and anneals to the wild type template upstream of the wild type region, using DNA polymerase and by polymerase chain reaction generates double stranded amplicons, which are then sequenced with the sequencing primer.

In certain clinical samples, such as cancer biopsy, the sample could have a heterogeneous cell population where some of the cells would have acquired somatic mutations, and where the number of cells with somatic mutations could be low compared the overwhelming number of wild type alleles. In such instances, there is a need to enrich the mutation template that will preferably enhance the detection of somatic mutations.

In another aspect of the above embodiment, in the amplification step, the lower primer anneals to the deletion template across the deletion region, thus selectively generating the deletion amplicons.

In another aspect of the above embodiment, in the sequencing step, two sequencing primers are used. One sequencing primer anneals to the wild type template where the 3' end of the sequencing primer anneals within the wild type region and remainder of the primer anneals upstream of the wild type region, so that the primer selectively sequences the wild type template. The second sequencing primer anneals to the deletion template where the sequencing primer binds across the deletion region, and where the 3' end of the sequencing primer anneals downstream of the deletion region and the 5' end of the sequencing primer anneals upstream of the deletion region, and hence selectively sequences the deletion template.

Further, the sequencing primer is designed in such a way that the last few nucleotides at the 3' end, for example 1, 2, 3, 4, 5, 6, 7, 8, 9, or 10 nucleotides, follow immediately after the deletion region, so that the entire sequencing primer is constructed so that it anneals to the deletion template and not to the wild type template.

In another aspect of the above embodiment, the upper primer carrying the detection region and the indicator region anneals to the wild type allele upstream of the wild type region and anneals to the deletion template upstream of the deletion region. Through polymerase chain reaction, the primer generates two single stranded DNA templates; the one from the wild type template will have a complete sequence, whereas the one from the deletion template will have single stranded DNA lacking the deletion region. The extended single stranded DNA templates are sequenced simultaneously using the same sequencing primer that anneals to the deletion template downstream of the deletion region and anneals to the wild type template downstream of the wild type region.

In another aspect of the above embodiment, in the amplification step a lower primer is included, which anneals to the deletion template downstream of the deletion region, and anneals to the wild type template downstream of the wild type region. Through polymerase chain reaction, the primer generates double stranded amplicons, both of which are sequenced using a sequencing primer.

In another aspect of the above embodiment, in the amplification step the upper primer at its 5' end carrying the detection region and the indicator region anneals to the deletion template across the deletion region, and through polymerase chain reaction, selectively generates the deletion amplicons.

In another aspect of the above embodiment, in the sequencing step, two sequencing primers are used. One sequencing primer anneals to the wild type template. The 3' end of this sequencing primer anneals within the wild type region and the remainder of the sequencing primer anneals downstream of the wild type region, so that it selectively sequences the wild type template. The second primer anneals to the deletion template. This sequencing primer anneals across the deletion region where its 3' end anneals upstream of the deletion region and its 5' end anneals downstream of the deletion region, and thus selectively sequences the deletion template.

In another aspect of the above embodiment, there is more than one deletion template, each with its own deletion region. By using mutant template-specific lower primers, and corresponding sequencing primers, locating the presence of mutant template specific indicator regions in the detection region identifies each of the deletion templates.

Figure 3:
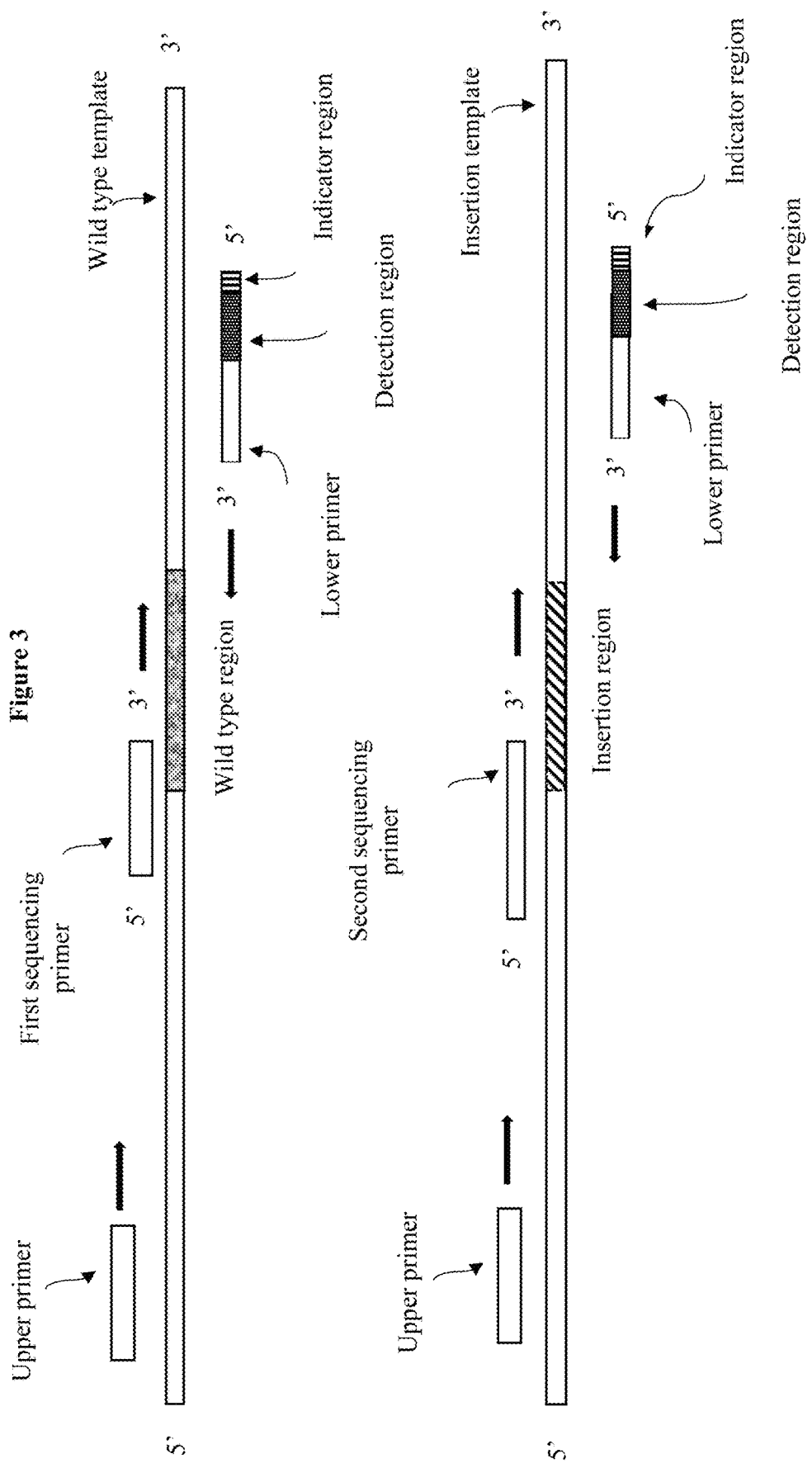
FIG. 3 illustrates the invention in identifying a mutant allele in a heterogeneous sample carrying an insertion segment compared to wild type allele; indicating the construction of the modified lower primer with detection region and the indicator region, PCR primer annealing sites and the sequencing primer annealing sites.
Figure 4:
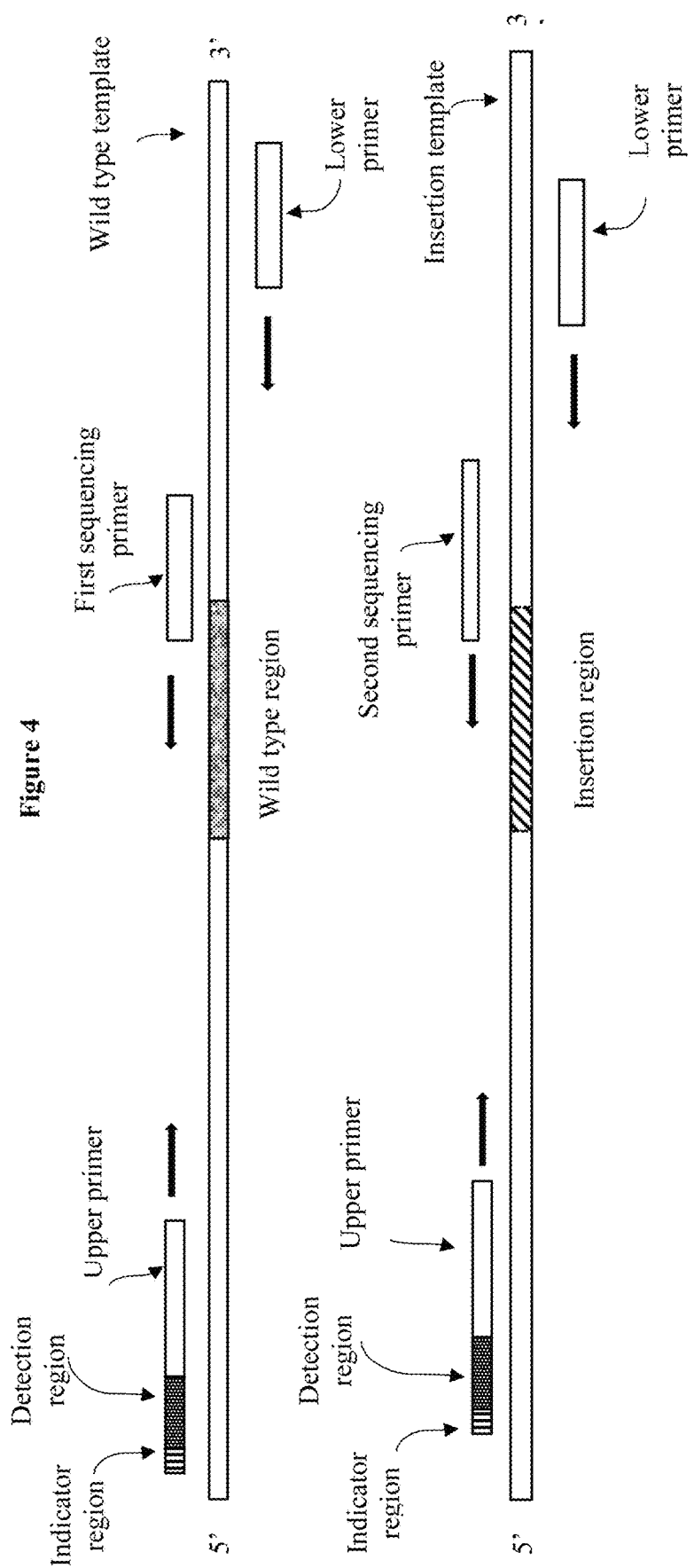
FIG. 4 illustrates the invention in identifying a mutant allele in a heterogeneous sample carrying an insertion segment compared to the wild type allele; indicating the construction of the modified upper primer with detection region and the indicator region, PCR primer annealing sites and the sequencing primer annealing sites.
Figure 5:
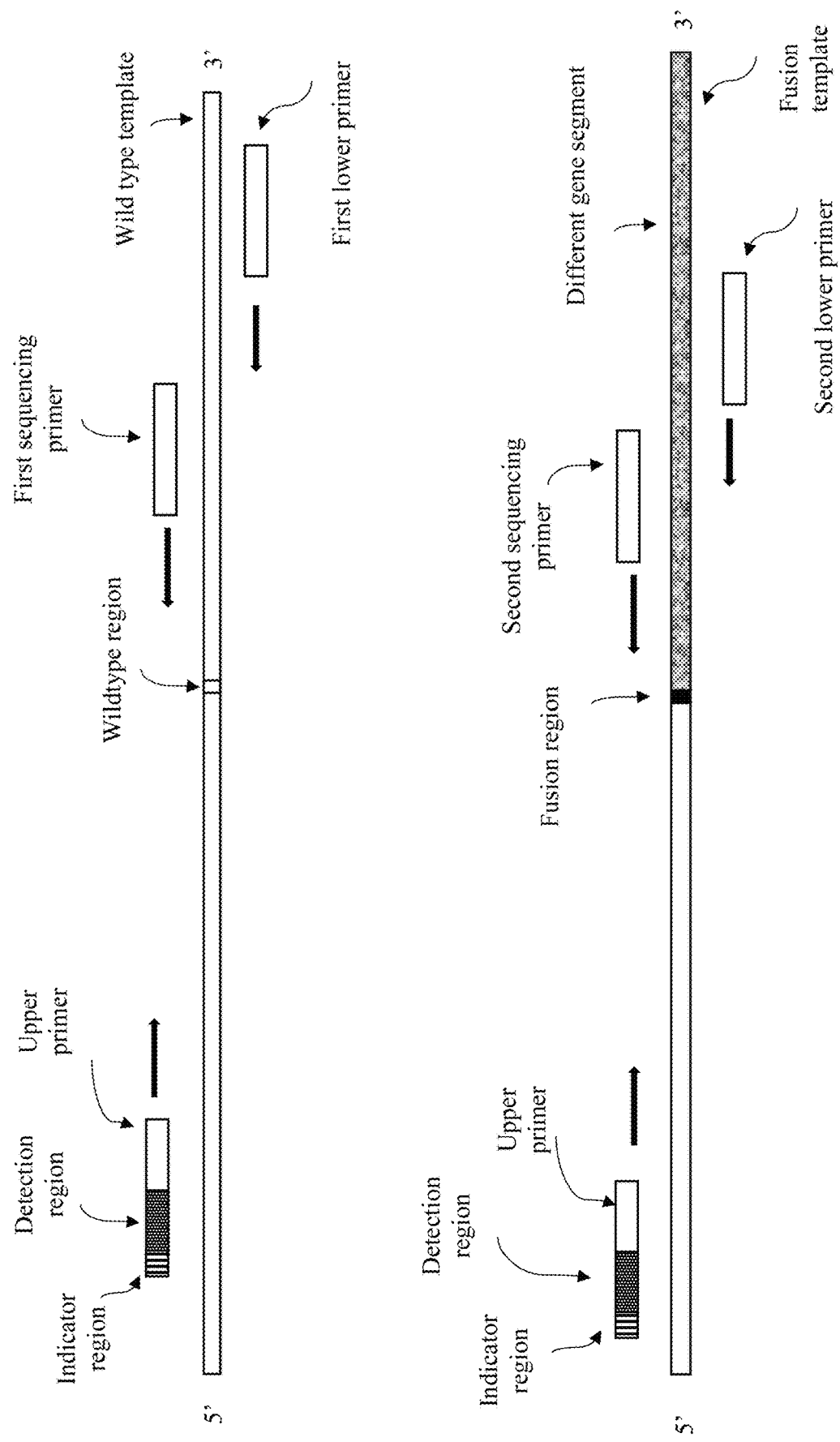
FIG. 5 illustrates the invention in identifying a mutant allele in a heterogeneous sample carrying a fusion gene compared to wild type allele; indicating the construction of the modified lower primer with detection region and the indicator region, PCR primer annealing sites and the sequencing primer annealing sites.

In another embodiment of the invention, one of the nucleic templates contains one or more additional nucleotides, known as an insertion template, compared to the corresponding wild type region of the wild type DNA template that that does not have the insertion region (FIGS. 3,4). The lower primer with the detection region and indicator region anneals to the insertion template downstream of the insertion region and anneals to the wild type template downstream of the wild type region, and through polymerase chain reaction, amplifies a segment of the DNA, generating corresponding single stranded amplicons. The wild type amplicons and insertion amplicons are sequenced simultaneously, using a sequencing primer that anneals to the extended insertion template upstream of the insertion region, anneals to the extended wild type template upstream of the wild type region, and generates two nucleotide sequences. The nucleotide generated from the insertion amplicon will be longer than the nucleotide sequence generated from the wild type amplicon. In this case, the indicator of the insertion region will be at the far end of the electropherogram, and the indicator region of the wild type will be within the detection region.

In another aspect of the above embodiment, in the amplification step, the lower primer with the detection region and indicator region anneals to the inserted template, where part of the 3' end of the lower primer anneals within the insertion region, and the remainder of the lower primer anneals downstream of the insertion region, and through polymerase chain reaction generates corresponding single stranded deletion amplicons.

In another aspect of the above embodiment, in the amplification step, the entire lower primer with the detection region and indicator region anneals within the insertion region and through polymerase chain reaction generates corresponding single stranded deletion amplicons.

In another aspect of the above embodiment, in the amplification step, the lower primer with the detection region and indicator region anneals to where part of its 5' end is within the inserted region and the remainder of the lower primer anneals downstream of the inserted region, and through polymerase chain reaction generates corresponding single stranded deletion amplicons.

In another aspect of the above embodiment, an upper primer that carries the detection and the indicator region at its 5' end, anneals to the insertion template upstream of the insertion region and anneals to the wild type template upstream of the wild type region, and through polymerase chain reaction amplifies a segment of the wild type template, generating corresponding single stranded DNA template, and amplifies a segment of the insertion template, generating corresponding single stranded DNA template. The wild type amplicons and insertion amplicons are sequenced simultaneously using a sequencing primer that anneals to the extended insertion template downstream of the insertion region, and anneals to the extended wild type template downstream of the wild type region, generating two nucleotide sequences; where the nucleotide generated from the insertion amplicon will be longer than the nucleotide sequence generated from the wild type. In this case, the indicator of the insertion region will be at the far end of the electropherogram, and the indicator region of the wild type will be within the detection region.

In another aspect of the above embodiment, in the amplification step, the upper primer carrying the detection region and indicator region anneals to the insertion template where part of the 5' end of the upper primer anneals upstream of the insertion region, and the remainder of the upper primer anneals within the insertion region, and through polymerase chain reaction amplifies a segment of the wild type template, generating a corresponding single stranded DNA template, and amplifies a segment of the insertion template, generating a corresponding single stranded DNA template.

In another aspect of the above embodiment, in the amplification step, the entire upper primer carrying the detection region and indicator region anneals within the insertion region, and through polymerase chain reaction amplifies a segment of the wild type template, generating corresponding single stranded DNA template and a segment of the insertion template, generating corresponding single stranded DNA template.

In another aspect of the above embodiment, in the amplification step, the upper primer carrying the detection region and indicator region, anneals where part of its 5' end anneals within the insertion region, and the remainder anneals downstream of the insertion region, and through polymerase chain reaction amplifies a segment of the wild type template, generating a corresponding single stranded DNA template, and amplifies a segment of the insertion template, generating a corresponding single stranded DNA template.

In another aspect of the above embodiment, in the amplification step, a lower primer anneals to the insertion template downstream of the insertion region and anneals to the wild type template downstream of the wild type region, generating corresponding double stranded amplicons.

In another aspect of the above embodiment, in the sequencing step, two sequencing primers are used, one sequencing primer anneals to the wild type, the other sequencing primer anneals to the insertion amplicons, with its 3' end annealing within the insertion region and its 5' end annealing upstream of insertion region.

In another aspect of the above embodiment, the sequencing primer anneals to the insertion amplicons, where the entire sequencing primer anneals within the insertion region.

In another aspect of the invention, in the sequencing step, the sequencing primer anneals to the insertion amplicons, with its 3' end annealing downstream of the insertion region and its 5' end annealing within the insertion region.

In another aspect of the above embodiment, there is more than one mutant template, each with its own insertion region. By using mutant template-specific lower primers, and corresponding sequencing primers, locating the presence of mutant template specific indicator regions in the detection region identifies each of the mutant templates.

Another example of the invention is, for example used in the identification of a single base substitution. Some of the clinical applications of the above inventions are described below. An example of genetic variations is nucleotide substitution. In humans the substitution could be a germline (hereditary) or somatic (acquired) mutation. An example of germline mutations includes mutation G20210A (Prothrombin), and Factor V Leiden that increase the likelihood for blood clotting. Another example of the clinical application includes detecting somatic mutations (acquired) including, for example, Braf p.V600E, a tyrosinase kinase mutation tested in late stage melanoma for treatment with vemurafenib, and the Epidermal growth factor receptor mutation (EGFR L858R).

In another embodiment of the invention, one of the alleles comprises a different nucleotide to that of the wild type, known as a substitution nucleotide, accrued by a substitution template, and the wild type is known as wild type nucleotide accrued by wild type template (FIG. 5). A lower primer with a detection and indicator region anneals to the substitution template downstream of the substitution nucleotide and anneals to the wild type template downstream of wild type nucleotide. Through polymerase chain reaction a segment of the wild type template is amplified, generating corresponding single stranded DNA template, and a segment of the substitution template is amplified, generating corresponding single stranded DNA template. Using two allele specific sequencing primers, the sequencing primer that anneals to the substitution nucleotide at its 3' end carries a nucleotide that is complimentary to the substitution nucleotide, and the sequencing primer that anneals to the wild type nucleotide at its 3; end carries nucleotide that is complimentary to the wild type nucleotide. The molecular weight of the sequencing primer that anneals to the substitution nucleotide is determined such that the indicator region of the substitution sequence falls within the detection region with the indicator region at the far end of the electropherogram. The method is the same as described above, but the sequencing step, for example, is modified. The sequencing step uses an allele specific nucleotide at the 3' end of the sequencing primer. The sequencing primer for the mutant allele comprises the mutant nucleotide at its 3' end and the wild-type comprises the wild type nucleotide at its 3' end. The molecular weight of one of the sequencing primers is different, hence the indicator sequence generated from the mutant allele appears within the detection region of the wild type.

In another aspect of the above embodiment, in the amplification step an upper primer is included, using DNA polymerase and by polymerase chain reaction generates double stranded amplicons, which are then sequenced with the sequencing primer.

In another aspect of the above embodiment, in the amplification step, an upper primer carrying the detection and indicator region anneals to the substitution template upstream of the substitution nucleotide and anneals to the wild type template upstream of wild type nucleotide. Using DNA polymerase and by polymerase chain reaction the primer amplifies a segment of the wild type template, generating a corresponding single stranded DNA template, and amplifies a segment of the substitution template, generating a corresponding single stranded DNA template. Using two allele specific sequencing primers, the sequencing primer that anneals to the substitution nucleotide at its 3' end carries a nucleotide that is complimentary to the substitution nucleotide, and the sequencing primer that anneals to the wild type nucleotide at its 3' end carries a nucleotide that is complimentary to the wild type nucleotide. The molecular weight of the sequencing primer that anneals to the substitution nucleotide is determined such that the indicator region of the substitution sequence falls within the detection region with the indicator region at the far end of the electropherogram.

In another aspect of the above embodiment, in the amplification step a lower primer is included, in addition to the upper primer, and through polymerase chain reaction generates double stranded amplicons, which are then sequenced with the sequencing primer.

In another embodiment, where the amplification is carried out through a ligase chain reaction that comprises a first upper primer that carries the detection region and the indicator region, and a first lower primer, which both anneal to the sense strand of the substitution template one nucleotide downstream of the substitution nucleotide, and anneals to the sense strand of the wild type template one nucleotide downstream of the wild type nucleotide, and comprises a second upper primer and a second lower primer, which both anneal to the anti-sense strand of the substitution template one nucleotide downstream of the substitution nucleotide, and anneal to anti-sense strand of the wild type template one nucleotide downstream of the wild type nucleotide. Amplification is through ligase chain reaction. Using two allele specific sequencing primers, the first sequencing primer anneals downstream of the substitution nucleotide, and at its 3' end carries a nucleotide that is complimentary to the substitution nucleotide. The second sequencing primer anneals downstream of the substitution, and at its 3' end carries a nucleotide that is complimentary to the wild type nucleotide. The molecular weight of the sequencing primer that anneals to the substitution nucleotide is determined such that the indicator region of the substitution sequence falls within the detection region, with the indicator region at the far end of the electropherogram.

In another aspect of the above embodiment the amplification is carried out ligase chain reaction that comprises a first upper primer and a first lower primer that carries the detection region and the indicator region, both annealing to the sense strand of the substitution template one nucleotide downstream of the substitution nucleotide, and annealing to the sense strand of the wild type template one nucleotide downstream of the wild type nucleotide. The reaction also comprises a second upper primer and second lower primer, which anneal to the anti-sense strand of the substitution template one nucleotide downstream of the substitution nucleotide and anneal to the anti-sense strand of the wild type template one nucleotide downstream of the wild type nucleotide. Amplification is through ligase chain reaction. Using two allele specific sequencing primers, the first sequencing primer anneals upstream of the substitution nucleotide, and at its 3' end carries a nucleotide that is complimentary to the substitution nucleotide. The sequencing primer anneals upstream of the substitution, and at its 3' end carries a nucleotide that is complimentary to the wild type nucleotide. The molecular weight of the sequencing primer that anneals to the substitution nucleotide is determined such that the indicator region of the substitution sequence falls within the detection region with the indicator region at the far end of the electropherogram.

Another clinical application of the invention includes the detection of gene fusion, for example Alk, ROS1, RET and NTRK (19, 20, 21, 22).

Figure 6:
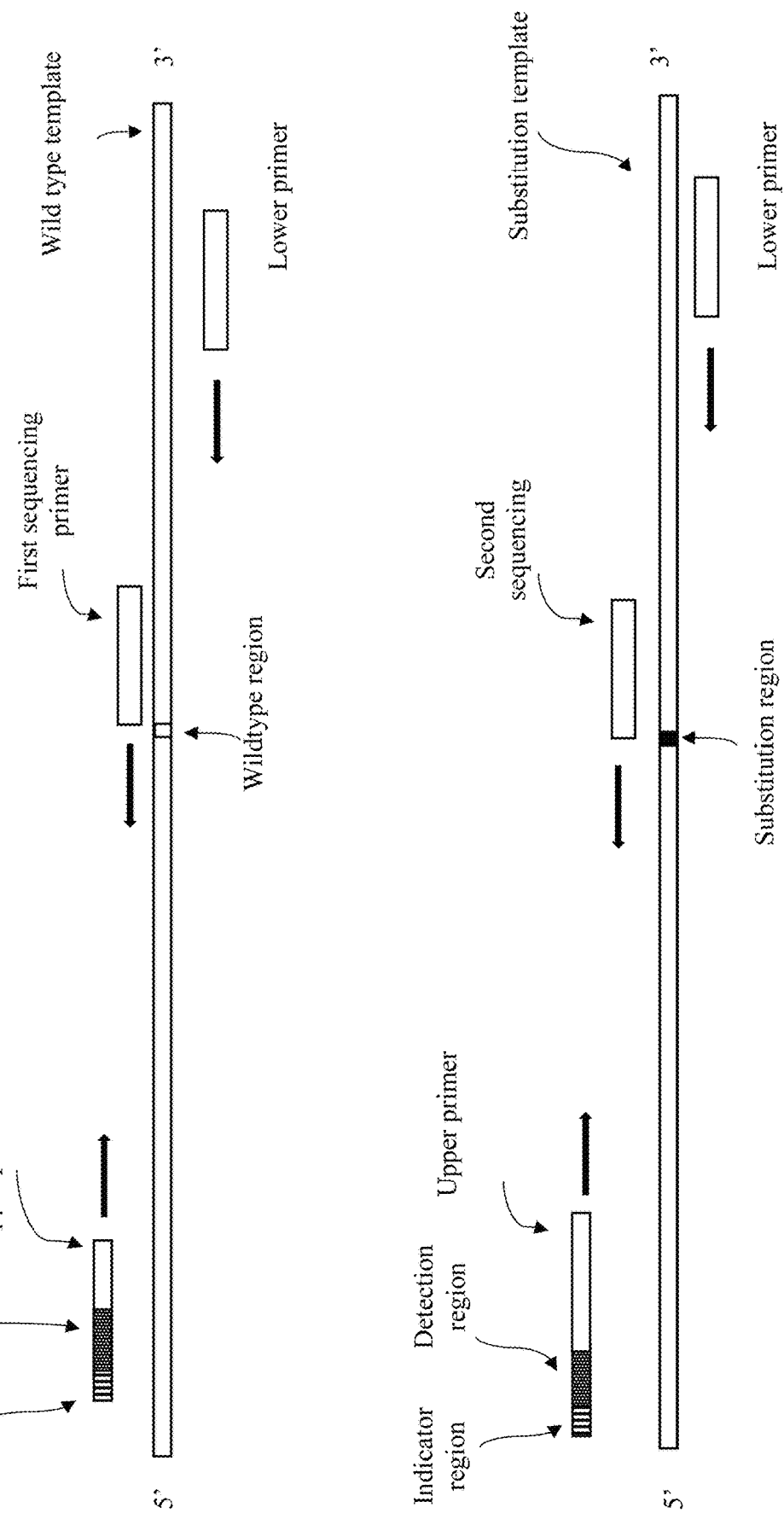
FIG. 6 illustrates the invention in identifying a mutant allele in a heterogeneous sample carrying a substitution nucleotide compared to wild type allele; indicating the construction of the modified lower primer with detection region and the indicator region, PCR primer annealing sites and the sequencing primer annealing sites.

An embodiment of the invention identifies a fusion template that comprises a segment A from one gene, joined at its 3' end to a 5' end of segment B from another gene, together known as a fusion region (FIG. 6). The corresponding wild type template contains a corresponding wild type region. Two lower primers are involved in amplification. One lower primer anneals to the sense strand of segment B of the fusion template downstream of the fusion region, and the other lower primer anneals to sense strand of segment C the wild type template downstream wild type region. Amplification is through polymerase chain reaction and sequencing is performed using a sequencing primer that anneals to segment A of the wild type amplicon and to segment A of the fusion amplicon. The primers that anneal to segment A of the wild type amplicon and segment A of the fusion amplicon at their 5' end comprise the detection region of repeated nucleotides, wherein the number of repeated nucleotides is identical or differ from each other, and an identification region is comprised of one or more repetitive nucleotides that are different to that of the detection region.

In another aspect of the above embodiment, the primers that anneal to segment C of the wild type template and segment B of the fusion template at its 5' end, comprise a detection region of repeated nucleotides, wherein the number of repeated nucleotides is identical or differ from each other, and an identification region is comprised of one or more repetitive nucleotides that are different to that of the detection region.

In another aspect of the above embodiment, double stranded amplicons of the fusion template and the wild type templates are generated using an additional set of primers that bind to the anti-sense strand, and through polymerase chain reaction the respective amplicons are sequenced.

In another aspect of the above embodiment, primers anneal across the fusion region in the fusion template, and/or the sequencing primer anneals to the fusion template across the fusion region in the fusion amplicon.

Another example of an application of the invention is detection of microbial species. Microbes are part and parcel of human health, some of which cause specific diseases. Infectious diseases that are common among human and animals are caused by viruses, bacteria, fungi, and protozoa. Further, such infections can be caused by multiple subspecies or subtypes that may cause the same disease. For example, sexually transmitted diseases caused by *Neisseria gonorrhea*, *Chlamydia trachomatis*. Another example would be human papillomavirus (HPV), which causes cancer of the cervix, for which there are thirteen subtypes that are identified with incidence of cancer of the cervix (23). Further, there are blood born infections caused, for example, by hepatitis B and hepatitis C, human immunodeficiency virus (HIV), and syphilis (*Treponema* palladium), for which screening is crucial for blood donations and transfusions. Other common infectious diseases include diarrhea caused by *Salmonella, typhimurium, Shigella* spp, Rota virus, epidemics caused by influenza viruses, and environmental contamination by *Giardia, Cryptosporidium*, and *E. coli*.

Moreover, the invention refers to a method for the detection of related microbial species. The instant invention is, for example, used in the identification of prokaryotic species and/or sub species. The detection process includes having a plasmid construct (Control template) with an insert DNA that serves the purpose of a reference template sequence and functions as an internal control. The principal of detection is that the number of nucleotides from the annealing locus at the 3' end of the sequencing primer to the indicator is genome specific. For example, for organism A, the number of nucleotides from the 3' end of the sequencing primer to the indicator is 28. For organism B the number of nucleotides from the 3' end of the sequencing primer to the indicator is 26.

Figure 7:
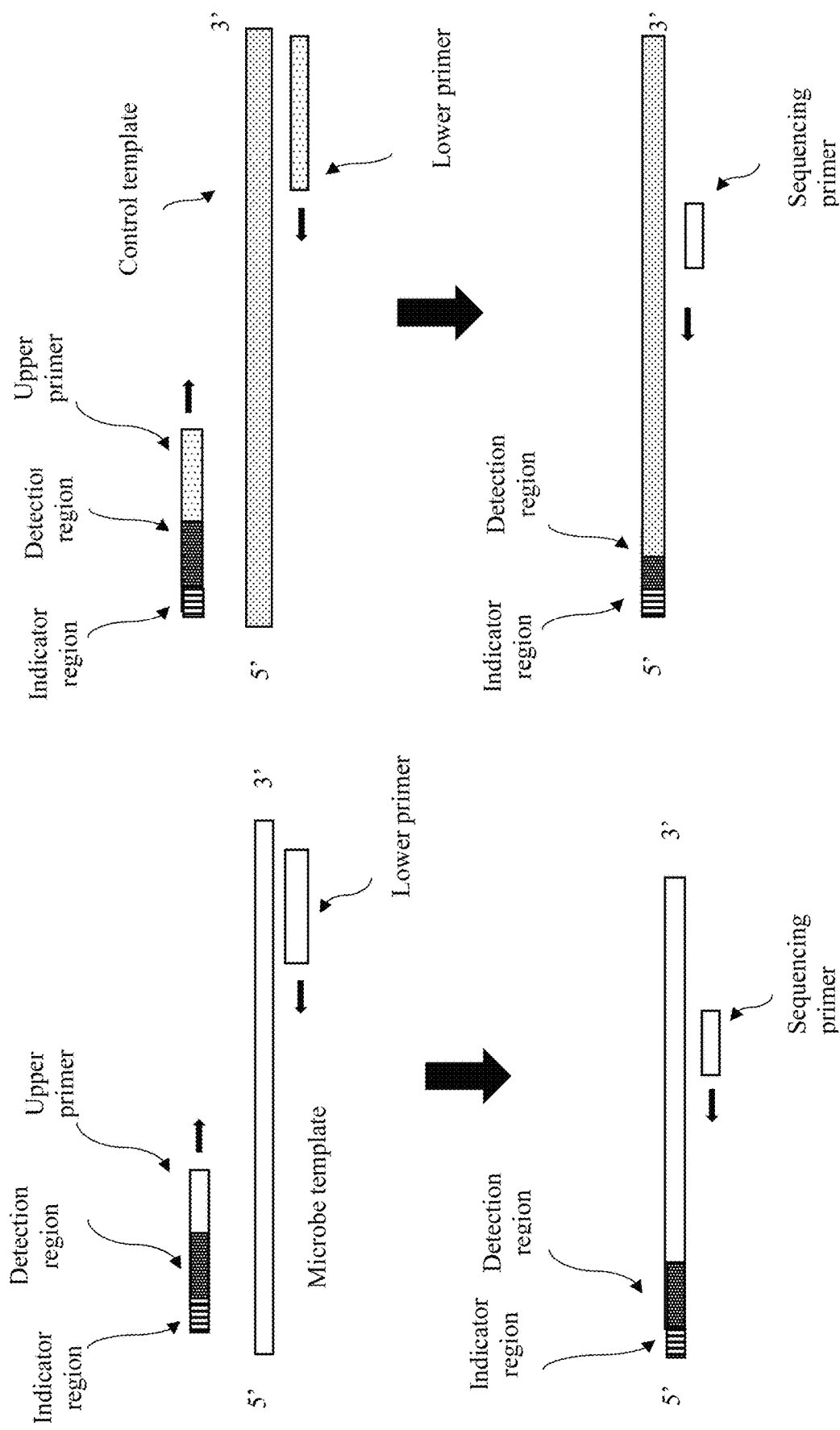
FIG. 7 illustrates the invention in identifying a microbial genome using a control template indicating the construction of the modified upper primer with detection region and the indicator region, PCR primer annealing sites and the sequencing primer annealing sites.

A species-specific lower primer anneals to the respective genomic template DNA and by extending in 3'-5' direction, amplifies a species-specific segment of the respective templates, generating single stranded amplicons (FIG. 7). The amplicons are sequenced using species-specific sequencing primers that anneal within the respective amplicon, generating a nucleotide sequence that is displayed on an electropherogram. If the pathogens are present, they are detected by the presence of a respective indicator region at the specified locus that overlaps with the signal in the detection region of the reference nucleotide sequence. If there are no pathogens present, this would indicate a negative sample, and the electropherogram will show only the reference sequence.

In another aspect of the above embodiment, in the amplification step, a set of species—specific upper primers are used, together with the lower primers, generating double stranded amplicons that are sequenced using species-specific sequencing primers, which anneal within the respective amplicon, generating a species specific nucleotide sequence that is displayed on an electropherogram. The homopolymer detection region and the indicator region could be carried by either the upper or lower primers.

In another aspect of the above embodiment, in the amplification step, the species-specific genomes are amplified using ligase chain reaction. This includes use of a species-specific first primer, and a second primer that at its 5' end contains a detection region and an indicator region of repeated nucleotides, wherein the number of repeated nucleotides is identical or differ from each other. The first primer and the second primer anneal to the sense DNA strand of the species-specific genomes. The amplification generates species-specific single stranded DNA that is complimentary to the corresponding species-specific genomic DNA templates. The single stranded amplicons are sequenced using species-specific sequencing primers that anneal within the single stranded amplicons, generating species specific nucleotide sequences, which are displayed on an electropherogram.

As another alternative, in the ligase amplification, an additional pair of the species-specific primers (third and fourth primers) are used that anneal to the anti-sense DNA strand of the species-specific genomes, hence generating double stranded amplicons. As an alternative, the detection region and the indicator region could be carried by either one of the first primers, in which case the sequencing primers will be the ones extending towards the modified region.

Other examples of the application of the invention also refer, for example, to the determination of micro satellite variants that are associated with human diseases. Hereditary nonpolyposis colorectal cancer (HNPCC), commonly referred as Lynch syndrome, is an autosomal hereditary condition that is associated with several cancers, including colorectal cancer. Lynch syndrome genetic changes occur, for example, in MLH1, MSH2, MSH6, or PMS2 or an EPCAM gene, and leads to defects in the DNA repair mechanism during cell replication. Genetic changes in MLHJ, MSH2, MSH6, or PMS2 or an EPCAM gene, are direct evidence of Lynch syndrome. There could be more than one mutation, some of which may not lead to defective repair. Hence, determination of defective repair is determined by its function. There are stretches of human DNA with single nucleotide repeats BAT 25, BAT 26 and dinucleotide repeats D2S123, D5S346, and D17S250. If there are genetic defects due to 25 mutations among MLH1, MSH2, MSH6, or PMS2 or EPCAM genes, this will be reflected in the number of repeats among repeats BAT 25, BAT 26 and dinucleotide repeats D2S123, D5S346, D17S250. The analysis and interpretation of these samples for MSI are challenging (9, 24).

Further, the invention is directed to the method for the detection of a trinucleotide variation found in Huntington's disease (25). The trinucleotide cytosine-adenine guanine (CAG) repeats in the Huntingtin gene exceeds about 39, which is considered a potential disease state and the individual will be affected. Early childhood detection of Huntington's disease could help in facilitating implementation of medical programs.

Further, the instant invention refers to the detection of splice variants. More than 50% of gene expression undergoes variations (splice variants) in their expression; some of the transcripts may lose one or more exons (26). Further, expression may also result either in addition of a few nucleotides at the exon:exon junction or in loss of a few nucleotides at the exon:exon junction. These variations in the transcript may result in proteins that may not have the epitope for their functionality, or if present, may not be accessible.

In an embodiment of the invention, the method relates to DNA fingerprinting. There are several loci in the human genome with repetitive nucleotide sequences known, for example, as short tandem repeats (STR). These STRs are, for example, segregated independently from each other and are used, as markers to characterize the human genome (27). Further, a number of such nucleotide repeats, can vary among the two alleles in the same individual. Analysis of STR has become a standard procedure in DNA fingerprinting. Application of DNA fingerprinting include, for example, forensic science and paternity testing. Other examples of genetic variations are in HER 2 exon 20 and/or MET exon 14, which together form a group of driver mutations in cancer (28, 29).

Another example of clinical application would be human papillomavirus (HPV), which causes cancer of the cervix. There are a number of subtypes of HPV that cause cancer of the cervix (23). This invention detects, for example, subtypes of human papilloma virus causing cancer of the cervix or Candida species causing vaginosis in women.

The invention comprises any number of primers, i.e., upper, lower and sequencing primer, in the method to detect one or more templates and/or different positions of a template. The method of the instant invention is used in assays to detect one or more DNA and/or RNA templates and the instant invention comprises such assays.

The instant invention is further directed to a kit for performing a method according to this invention, wherein the kit comprises one or more upper and/or lower primer(s), a sequencing primer, and optionally, a reference sequence for detecting a DNA and/or RNA templates.

EXAMPLES

The following examples illustrate different embodiments of the present invention, but the invention is not limited to these examples.

Example 1: Detection of Epidermal Growth Factor Receptor (e.g. deletion in EGFR exon 19) Each PCR reaction included 25.0 µl of 2× buffer (MultiPlex PCR Master Mix, Qiagen). 1.0 µl each of the 10 pmol forward and reverse primers (Bio-ID Diagnostics Inc, Canada) were added with 10 ng of DNA extract from Formalin Fixed Paraffin Embedded Tissue (FFPE). An appropriate amount of water was added to bring the final volume to 50.0 PCR conditions: 95° C./5 min, (95° C./30 sec, 57.5° C./90 sec, 72° C./30 sec)×35, 68° C./10 min. Following PCR clean up, sequencing reaction was set up using 1.0 µl of Big dye, 9.5 µl of 5× sequencing buffer, 1 pmoles of sequencing primer (Bio-ID Diagnostics Inc, Canada) and 30 µl of the purified PCR products and 4.5 µl of Dnase free water to a total reaction volume of 50 µl. Cycle sequencing conditions: (96° C./15 sec, 55° C./10 sec, 60° C./2.5 min)×25. Cycle sequencing products were cleaned with CleanSEQ (Beckman Agencourt, USA) and eluted in 40 µl of Dnase free water. The cleaned products were injected for 16 seconds into the ABI Genetic Analyzer 3130xl, and the electropherogram was analyzed using ABI Sequencing Analysis Software 6.0. The electropherogram shows wild type with EGFR deletion.

Example 2: Determination of Microsatellite Variances

Determination of micro satellite variances that are associated with human diseases. Hereditary nonpolyposis colorectal cancer (HNPCC), commonly referred as Lynch Syndrome, is an autosomal hereditary condition that is associated with several cancers, including colorectal cancer. The PCR primers are designed so that the lower primer has a repeat adenosine nucleotide with guanidine as the last nucleotide. The target segment is amplified using an upper primer and a modified lower primer. PCR products are cleaned and sequenced using a sequencing primer upstream of the region of the microsatellite variant. The cycle sequencing mixture is purified and analyzed through capillary electrophoresis.

Each PCR reaction included 25.0 µl of 2× buffer (MultiPlex PCR Master Mix, Qiagen). 1.0 µl each of the 10 pmol forward and reverse primers (Bio-ID Diagnostics Inc, Canada) were added to the reaction with 1.0 µl of the corresponding control clone. An appropriate amount of water was added to bring the final volume to 50.0 1. PCR conditions: 95C/5 min, (95C/30 sec, 57.5C/90 sec, 72C/30 sec)×35, 68C/10 min. Following PCR clean up, the sequencing reaction was set up using 1.0 µl of Big dye, 9.5 µl of 5× sequencing buffer, 1.0 pmoles of sequencing primer (Bio-ID Diagnostics Inc, Canada) and 30 µl of the purified PCR products and 4.5 µl of Dnase free water to a total reaction volume of 50 µl. Cycle sequencing conditions: (96C/15 sec, 55C/10 sec, 60C/2.5 min)×25. Cycle sequencing products were cleaned with CleanSEQ (Beckman Agencourt USA) and eluted in 40 µl of Dnase free water. The cleaned products were injected for 16 sec into ABI Genetic analyzer 3130xl and the electropherogram was analyzed using ABI Sequencing Analysis software 6.0. The electropherogram showed the wild type indicator as well as the deleted region (see FIGS. 6 and 10 7).

Example 3: Determination of Microbial Speciation

Disease condition: Sexually transmitted disease in human. Pathogens tested: *Chlamydia trachomatis, Neisseria gonorrhea* with internal control ICD.

Each PCR reaction included 25.0 µl of 2× buffer (Multi-Plex PCR Master Mix, Qiagen). 1.0 µl each of the 10 pmol forward and reverse primers (Bio-ID Diagnostics Inc, Canada) were added to the reaction with 2.0 µl of the corresponding control clones (ICD –0.24 ng/ul, GC-0.42 ng/ul, CT-0.25 ng/ul). An appropriate amount of water was added to bring the final volume to 50.0 µPCR conditions: 95° C./5 min, (95° C./30 sec, 60° C./90 sec, 72° C./45 sec)×35, 25° C./hold. Following PCR cleanup, a sequencing reaction was set up using 1.0 µl of Big dye, 3.5 µl of 5× sequencing buffer, 3 pmoles of sequencing primers (Bio-ID Diagnostics Inc, Canada) and 5 µl of the purified PCR products and 1.5 ml of Dnase free water to a total reaction volume of 20 µl. Cycle sequencing conditions: (96° C./15 sec, 62° C./45 sec)×25. Cycle sequencing products were cleaned with CleanSEQ (Beckman Agencourt USA) and eluted in 40 µl of Dnase free water. The cleaned products were injected for 16 sec into ABI Genetic analyzer 3130xl and the electropherogram was analyzed using ABI Sequencing Analysis Software 6.0.
Concept of Primers:

REFERENCE CITED

Us Patent Documents

1. U.S. Pat. No. 9,005,425 Burrows et al
2. U.S. Pat. No. 8,771,965 Sarkar et al
3. U.S. Pat. No. 8,754,191 Nielsen et al
4. U.S. Pat. No. 8,828,391 Denis, et al—EGFR
5. U.S. Pat. No. 8,788,215 Chakraborty et al—STR Other Publications 1. Marie B., et al. Assessment of EGFR Mutation Status in Lung Adenocarcinoma by Immunohistochemistry Using Antibodies Specific to the Two Major Forms of Mutant EGFR. Journal of Molecular Diagnostics, 2010.Vol. 12, No. 2, March
2. Nyren, Petersson and Uhlen (1993) "Solid Phase DNA Minisequencing by an Enzymatic Luminometric Inorganic Pyrophosphate Detection Assay" Analytical Biochemistry 208 (1), 171-175
3. Sam Behjati and Patrick S Tarpey What is next generation sequencing? *Arch Dis Child Educ Pract Ed.* 2013 December; 98(6): 236-238.
4. Choi, Y W et al. EGFR Exon 19 Deletion is Associated with Favorable Overall Survival After First-line Gefitinib Therapy in Advanced Non-Small Cell Lung Cancer Patients. *Am J Clin Oncol.* 2018 April; 41(4):385-390.
5. Banavali, Nilesh K. "Partial Base Flipping is Sufficient for Strand Slippage near DNA Duplex Termini". *Journal of the American Chemical Society.* (2013), 135 (22): 8274-8282.13
6. Richard Bayliss, Molecular mechanisms that underpin EML4-ALK driven cancers and their response to targeted drugs. *Cell Mol Life Sci.* 2016; 73: 1209-1224.
7. Bollag G, Tsai J, Zhang J, Zhang C, Ibrahim P, Nolop K, Hirth). "Vemurafenib: the first drug approved for BRAF-mutant cancer". *Nature Reviews Drug Discovery.* P (November 201211 (11): 873-886.
8. Steven Belenko, Detecting, Preventing, and Treating Sexually Transmitted Diseases Among Adolescent Arrestees: An Unmet Public Health Need. Am J Public Health. 2009 June; 99(6): 1032-1041. doi: 10.2105/AJPH.2007.122937
9. Pagin, A, F Zerimech, J Leclerc, A Wacrenier, S Lejeune, C Descarpentries, F Escande, N Porchet, M-P Buisine. Evaluation of a new panel of six mononucleotide repeat markers for the detection of DNA mismatch repair deficient tumors. *British Journal of Cancer volume* 108, pages 2079-2087 28 May 2013.
10. https://assets.thermofisher.com/TFS-Assets/BID/brochures/kingfisher-instruments-experience-brochure.pdf.
11. Saiki, R.; Scharf, S.; Faloona, F.; Mullis, K.; Horn, G.; Erlich, H.; Arnheim, N. "Enzymatic amplification of beta-globin genomic sequences and restriction site analysis for diagnosis of sickle cell anemia".(1985). Science. 230 (4732): 1350-1354.
12. Wiedmann, M; Wilson, W J; Czajka, J; Luo, J; Barany, F; Batt, C A "Ligase chain reaction (LCR)—overview and applications". (February 1994). PCR Methods and Applications. 3 (4): S51-64.
13. Bustin S A, Benes V, Garson J A, Hellemans J, Huggett J, Kubista M, Mueller R, Nolan T, Pfaffl M W, Shipley G L, Vandesompele J, Wittwer C T "The MIQE guidelines: minimum information for publication of quantitative real-time PCR experiments". Clinical Chemistry. (2009). 55 (4): 611-22.
14. Pollack J R; Perou C M; Alizadeh A A; Eisen M B; Pergamenschikov A; Williams C F; Jeffrey S S; Botstein D; Brown P O "Genome-wide analysis of DNA copy-number changes using cDNA microarrays". (1999). Nat Genet. 23 (1): 41-46
15. Pettersson E, Lundeberg J, Ahmadian A (February 2009). "Generations of sequencing technologies". Genomics. 93 (2): 105-11.
16. Southern, Edwin Mellor "Detection of specific sequences among DNA fragments separated by gel electrophoresis". (5 Nov. 1975). *Journal of Molecular Biology.* 98 (3): 503-517.
17. Chehap et al., A dimorphic 4-bp repeat in the cystic fibrosis gene is in absolute linkage disequilibrium with the delta F508 mutation: implications for prenatal diagnosis and mutation origin. Am J Hum Genet. 1991 February; 48(2): 223-226.
18. Norikazu Matsuo. Association of EGFR Exon 19 Deletion and 5 EGFR-TKI Treatment Duration with Frequency of T790M Mutation in EGFR-Mutant Lung Cancer Patients. Sci Rep. 2016; 6: 36458.
19. Shaw, A. T and Jeffrey A. Engelman. ALK in Lung Cancer: Past, Present, and 15 Future. J Clin Oncol. 2013 Mar. 10; 31(8): 1105-1111.
20. Bubendorf, L et al., Testing for ROS1 in non-small cell lung cancer: a review with recommendations. Virchows Arch. 2016; 469(5): 489-503.

21. Snehal Dabir et al., RET Mutation and Expression in Small-Cell Lung Cancer. Journal of Thoracic Oncology. Volume 9, Issue 9, September 2014, Pages 1316-1323
22. Su Jin Lee et al., NTRK gene amplification in patients with metastatic cancer. Precision and Future Medicine 2017; 1(3): 129-137.
23. Li K, Yin R, Wang D, Li Q. Human papillomavirus subtypes distribution among 2309 cervical cancer patients in West China. Oncotarget. 2017 Apr. 25; 8(17):28502-28509. doi: 10.18632/oncotarget.16093.
24. G Perinchery, D Nojima, R Goharderakhshan, Y Tanaka, J Alonzo, R Dahiya Microsatellite instability of dinucleotide tandem repeat sequences is higher than 30 trinucleotides, tetranucleotide and pentanucleotide repeat sequences in prostate cancer. International Journal of Oncology. Jun. 1, 2000, Pages:1203-1212 https://doi.org/10.3892/ijo.16.6.1203.
25. Oliver J, et al., Reduced penetrance alleles for Huntington's disease: a multi-center direct observational study. J Med Genet. 2007 March; 44(3): e68.
26. Sartor O, Dong Y. Androgen receptor variant 7: an important predictive biomarker in castrate resistant prostate cancer. Asian J Androl. 2015 May-June; 17(3):439-40. doi: 10.4103/1008-682X.145069.
27. McNamara-Schroeder K, Olonan C, Chu S, Montoya M C, Alviri M, Ginty S, Love J. J. DNA fingerprint analysis of three short tandem repeat (STR) loci for biochemistry and forensic science laboratory courses. Biochem. Mol. Biol. Educ. 2006 September; 34(5):378-83. Doi:10.1002/bmb.2006.494034052665.
28. Kosaka, T et al., Response heterogeneity of EGFR and HER2 exon 20 insertions to covalent EGFR and HER2 inhibitors. Cancer Res. 2017 May 15; 77(10): 2712-2721.
29. Reungwetwattana. T and Sai-Hong Ignatius Ou. MET exon 14 deletion (METex14): finally, a frequent-enough actionable oncogenic driver mutation in non-small cell lung cancer to lead MET inhibitors out of "40 years of wilderness" and into a clear path of regulatory approval. Transl Lung Cancer Res. 2015 December; 4(6): 820-824.

EGFR PCR primers
Upper primer
(SEQ ID NO: 1)
5'-GTG TGA TTC GTG GAG CCC AAC AG-3'

Lower primer
(SEQ ID NO: 2)
5'-GTATTATTATTATTATTATTATTACTC ACA TCG AGG ATT TCCTTG TTG GC Sequencing primer:
Mutant
(SEQ ID NO: 3)
5' CTC ACA TCG AGG ATT TCC TTG TTG GC-3'

Wild type:
(SEQ ID NO: 4)
5' ^-AAAGTTAAAATTCCCGTCGCTATCAAGG-3'

Control primers
PCR upper primer:
(SEQ ID NO: 5)
5' AAAAGGGGTTTTCTTAAGCGTCGATGGAGGAGTTTGTAA ATGA AG-3'

PCR Lower primer:
(SEQ ID NO: 6)
5'-TCAAAGAATGGTCCTGCACCAGTAATATGC-3'

Sequencing primer:
(SEQ ID NO: 7)
5'-^-CCAGTTGACTGCAGACCTGTATCGTAATGAAC-3'

*Chlamydia trachomatis*,
PCR upper primer:
(SEQ ID NO: 8)
5'-TCGGTTTTGATAATTTGTCCTTAACTTGGGAATAACGGTTGG-3'

PCR Lower primer:
(SEQ ID NO: 9)
5'-CCCTAGAGCCTTCATCACACACGCG-3'

Sequencing primer:
(SEQ ID NO: 10)
5'-TATGCCCAAATATCGCCACATTCGGTATTAGCGG-3'

*Neisseria gonorrhea*
PCR upper primer:
(SEQ ID NO: 11)
5'-GCTTTCGGCGAGGATTTGTACGAAGAGCTG-3'

PCR Lower primer:
(SEQ ID NO: 12)
5'-TTGCCCGCGCCGTTGATACCG-3'

Sequencing primer:
(SEQ ID NO: 13)
5'-^-CCCATATCGCCGGTAATCAGCACGG-3'

The invention claimed is:

1. A method of identifying germline and somatic mutations in a heterogenous sample that carries a template nucleic acid with a mutation region of at least one nucleotide relative to a corresponding wild type template known as the wild type region of a eukaryotic genome;
   a) using a primer pair comprising an upper primer and a lower primer, wherein one of the lower primer or upper primer comprises a 5' tail sequence comprising:
      (i) a detection region of one or more repetitive nucleotide sequences comprising NNX or XXN, wherein N is a first nucleotide and X is a second nucleotide different from the first nucleotide; and
      (ii) an indicator region 5' of the detection region with one or more repetitive nucleotides YY, wherein Y is a nucleotide different from N and X, and
   b) using DNA polymerase or DNA ligase, the primer pair flanks the mutation in the mutation template and amplifies a segment of the mutation template encompassing the mutation region, generating a mutation amplicon by polymerase chain reaction, and
   amplifies a segment of the wild type template encompassing the wild type region, generating a wild type amplicon by polymerase and/or by ligase chain reaction, the mutation template and the wild type amplicons comprising the detection region and the indicator region, and
   c) sequencing both the wild type amplicons and the mutation amplicons simultaneously using a sequencing primer that comprises a primer selected from the group consisting of a primer that anneals to the wild type amplicon upstream of the wild type region, a primer that anneals to the mutation amplicon upstream of the mutation region, a primer that comprises a 3' end that anneals downstream of the mutation region and a 5' end that anneals upstream of the mutation region and a primer that comprises a 3' end that anneals upstream of the mutation region and a 5' end that anneals downstream of the mutation region, and
   by dideoxy chain termination method, and capillary electrophoresis, generates two nucleotide sequences that are automatically aligned and displayed on an electropherogram, and
   determining that a mutation is present in the sample when a mutation template read sequence comprises a shifted detection region and a shifted indicator region compared to the wild type template read sequence.

2. A kit for identifying germline and somatic mutations in a heterogenous sample that carries a template nucleic acid with a mutation region of at least one nucleotide relative to a corresponding wild type template known as the wild type region of a eukaryotic genome, the kit comprising:
   (1) a primer pair comprising an upper primer and a lower primer, wherein one of the lower primer or upper primer comprises a 5' tail sequence comprising:
      (i) a detection region of one or more repetitive nucleotides sequences comprising NNX or XXN, wherein N is a first nucleotide and X is a second nucleotide different from the first nucleotide; and
      (ii) an indicator region 5' of the detection region with one or more repetitive nucleotides YY, wherein Y is a nucleotide different from N and X; and
   (2) a sequencing primer that comprises a primer selected form the group consisting of a primer that anneals to a wild type amplicon upstream of the wild type region, a primer that anneals to a mutation amplicon upstream of the mutation region, a primer that comprises a 3' end that anneals downstream of the mutation region and a 5' end that anneals upstream of the mutation region and a primer that comprises a 3' end that anneals upstream of the mutation region and a 5' end that anneals downstream of the mutation region.

3. A method of identifying microbial genomes, with a synthetic control DNA template as reference template, and a) using a first pair of primers for the microbial genome and a second pair of primers for the control template, wherein the first pair of primers and the second pair of primers each comprise an upper primer and a lower primer, wherein one of the lower primer or upper primer comprises a 5' tail sequence comprising:
  (i) a detection region of one or more repetitive nucleotides sequences comprising NNX or XXN, wherein N is a first nucleotide and X is a second nucleotide different from the first nucleotide; and
  (ii) an indicator region 5' of the detection region with one or more repetitive nucleotides YY, wherein Y is a nucleotide different from N and X, and
c) using DNA polymerase or DNA ligase the first primer pair flanks and amplifies a segment of the microbial genome generating an amplicon by polymerase chain reaction or ligase chain reaction, and the second primer pair for the control DNA template amplifies a segment of control DNA template generating an amplicon by polymerase chain reaction or ligase chain reaction comprising the detection region and the indicator region, and
c) simultaneously sequencing by dideoxy chain termination method and capillary electrophoresis, the microbial amplicons using a microbial sequencing primer and the control DNA amplicons using a control DNA amplicon sequencing primer, to generate nucleotide sequences that are automatically aligned and displayed on an electropherogram, and confirming the presence of specific microbial genomes by identifying pre-determined microbial genome specific locus of the indication regions, in the detection region of the control DNA template.

4. A kit for identifying a microbial genome and a control DNA template comprising
  (1) a first pair of primers that hybridizes to the microbial genome comprising an upper primer and a lower primer, and a second pair of primers that hybridize to the control DNA template, wherein in each of the first primer pair and the second primer pair one of the lower primer or upper primer comprises a 5' tail sequence comprising:
    (i) a detection region of one or more repetitive nucleotides sequences comprising NNX or XXN, wherein N is a first nucleotide and X is a second nucleotide different from the first nucleotide; and
    (ii) an indicator region 5' of the detection region with one or more repetitive nucleotides YY, wherein Y is a nucleotide different from N and X; and
  (2) a microbial sequencing primer that comprises a primer that anneals to the microbial amplicon and a control DNA template sequencing primer that anneals to the control DNA amplicon.

* * * * *